US012661187B2

(12) United States Patent
Wilson et al.

(10) Patent No.: US 12,661,187 B2
(45) Date of Patent: Jun. 23, 2026

(54) ENDOVASCULAR VALVE FORMATION SYSTEM WITH IMAGING CAPABILITY

(71) Applicant: INTERVENE, INC., Redwood City, CA (US)

(72) Inventors: Fletcher T. Wilson, San Francisco, CA (US); Michi E. Garrison, Half Moon Bay, CA (US); Kent D. Dell, Redwood City, CA (US); Herbert Mendoza, South San Francisco, CA (US); Benjamin J. Clark, Redwood City, CA (US); Emmanuelle F. Pease, San Francisco, CA (US)

(73) Assignee: INTERVENE, INC., Redwood City, CA (US)

( * ) Notice: Subject to any disclaimer, the term of this patent is extended or adjusted under 35 U.S.C. 154(b) by 0 days.

(21) Appl. No.: 18/458,358

(22) Filed: Aug. 30, 2023

(65) Prior Publication Data

US 2024/0164849 A1     May 23, 2024

Related U.S. Application Data

(63) Continuation of application No. 17/355,459, filed on Jun. 23, 2021, now Pat. No. 11,771,501.
(Continued)

(51) Int. Cl.
*A61B 34/20*          (2016.01)
*A61B 8/00*          (2006.01)
(Continued)

(52) U.S. Cl.
CPC ................ *A61B 34/20* (2016.02); *A61B 8/12* (2013.01); *A61B 8/4254* (2013.01); *A61B 8/445* (2013.01);
(Continued)

(58) Field of Classification Search
None
See application file for complete search history.

(56) References Cited

U.S. PATENT DOCUMENTS 3,704,711  A     12/1972  Park
4,794,931  A      1/1989  Yock
(Continued)

FOREIGN PATENT DOCUMENTS

CA          1281381  C      3/1991
CA          2678971  A1     8/2008
(Continued)

OTHER PUBLICATIONS

Corcos, I., "A new autologous venous valve by intimal flap: One cases report." Note Di Tecnica, Minerva Cardioangiol, 2003, 51, 10 pages.
(Continued)

*Primary Examiner* — Keith M Raymond
*Assistant Examiner* — Ashish S. Jasani
(74) *Attorney, Agent, or Firm* — Perkins Coie LLP

(57)          ABSTRACT

Endovascular valve formation systems with imaging capabilities and associated devices and methods are disclosed herein. In some embodiments, a valve formation and imaging system can include, for example, (i) a valve formation device configured to access a vessel wall and dissect a portion of the vessel wall to form an autologous valve leaflet and (ii) an imaging device configured to image the vessel wall and components of the valve formation device during a valve formation procedure. In some embodiments, the imaging device is integrated into a distal end portion of the valve formation device. In some embodiments, the imaging device is a separate catheter device positionally coupled to the valve formation device and/or components thereof.

17 Claims, 10 Drawing Sheets

Related U.S. Application Data

(60) Provisional application No. 63/043,087, filed on Jun. 23, 2020.

(51) Int. Cl.

| | |
|---|---|
| *A61B 8/12* | (2006.01) |
| *A61B 17/00* | (2006.01) |
| *A61M 25/00* | (2006.01) |
| *A61M 25/01* | (2006.01) |

(52) U.S. Cl.
CPC ... *A61B 17/00234* (2013.01); *A61M 25/0082* (2013.01); *A61M 25/0136* (2013.01); *A61M 25/003* (2013.01); *A61M 2025/0166* (2013.01)

(56)                References Cited

U.S. PATENT DOCUMENTS

| | | | |
|---|---|---|---|
| 4,898,574 A | 2/1990 | Uchiyama et al. |
| 4,932,962 A | 6/1990 | Yoon et al. |
| 5,112,339 A | 5/1992 | Zelman |
| 5,190,046 A | 3/1993 | Shturman |
| 5,372,601 A | 12/1994 | Lary |
| 5,443,443 A | 8/1995 | Shiber |
| 5,464,395 A | 11/1995 | Faxon et al. |
| 5,601,588 A | 2/1997 | Tonomura et al. |
| 5,606,975 A | 3/1997 | Liang et al. |
| 5,695,507 A | 12/1997 | Auth et al. |
| 5,738,901 A | 4/1998 | Wang et al. |
| 5,795,322 A | 8/1998 | Boudewijn |
| 5,810,847 A | 9/1998 | Laufer et al. |
| 5,836,945 A | 11/1998 | Perkins |
| 5,882,340 A | 3/1999 | Yoon |
| 5,989,276 A | 11/1999 | Houser et al. |
| 6,190,353 B1 | 2/2001 | Makower et al. |
| 6,302,870 B1 | 10/2001 | Jacobsen et al. |
| 6,344,027 B1 | 2/2002 | Goll |
| 6,375,635 B1 | 4/2002 | Moutafis et al. |
| 6,379,319 B1 | 4/2002 | Garibotto et al. |
| 6,458,098 B1 | 10/2002 | Kanesaka |
| 6,475,226 B1 | 11/2002 | Belef et al. |
| 6,506,178 B1 | 1/2003 | Schubart et al. |
| 6,514,217 B1 | 2/2003 | Selmon et al. |
| 6,524,251 B2 | 2/2003 | Rabiner et al. |
| 6,676,665 B2 | 1/2004 | Foley et al. |
| 6,685,648 B2 | 2/2004 | Flaherty et al. |
| 6,692,466 B1 | 2/2004 | Chow et al. |
| 6,702,744 B2 | 3/2004 | Mandrusov et al. |
| 6,726,677 B1 | 4/2004 | Flaherty et al. |
| 6,758,836 B2 | 7/2004 | Zawacki |
| 6,902,576 B2 | 6/2005 | Drasler et al. |
| 7,008,411 B1 | 3/2006 | Mandrusov et al. |
| 7,056,325 B1 | 6/2006 | Makower et al. |
| 7,150,738 B2 | 12/2006 | Ray et al. |
| 7,179,249 B2 | 2/2007 | Steward et al. |
| 7,273,469 B1 | 9/2007 | Chan et al. |
| 7,357,795 B2 | 4/2008 | Kaji et al. |
| 7,517,352 B2 | 4/2009 | Evans et al. |
| 7,775,968 B2 | 8/2010 | Mathis |
| 7,780,592 B2 | 8/2010 | Tronnes |
| 7,918,870 B2 | 4/2011 | Kugler et al. |
| 7,927,305 B2 | 4/2011 | Yribarren et al. |
| 7,931,594 B2 | 4/2011 | Hirsh |
| 7,938,819 B2 | 5/2011 | Kugler et al. |
| 7,955,346 B2 | 6/2011 | Mauch et al. |
| 8,025,655 B2 | 9/2011 | Kugler et al. |
| 8,083,726 B1 | 12/2011 | Wang |
| 8,083,727 B2 | 12/2011 | Kugler et al. |
| 8,100,860 B2 | 1/2012 | Von et al. |
| 8,114,123 B2 | 2/2012 | Brenzel et al. |
| 8,177,748 B1 | 5/2012 | Beyerlein |
| 8,177,802 B2 | 5/2012 | Mauch et al. |
| 8,267,947 B2 | 9/2012 | Pantages et al. |
| 8,323,261 B2 | 12/2012 | Kugler et al. |
| 8,460,316 B2 | 6/2013 | Wilson et al. |
| 8,636,712 B2 | 1/2014 | Kugler et al. |
| 8,753,366 B2 | 6/2014 | Makower et al. |
| 9,320,504 B2 | 4/2016 | Wilson et al. |
| 9,381,034 B2 | 7/2016 | Karwei |
| 9,545,289 B2 | 1/2017 | Wilson et al. |
| 9,814,538 B2 | 11/2017 | Wilson et al. |
| 9,827,005 B2 | 11/2017 | Wilson et al. |
| 9,949,752 B2 | 4/2018 | Wilson et al. |
| 9,955,990 B2 | 5/2018 | Wilson et al. |
| 10,105,157 B2 | 10/2018 | Wilson et al. |
| 10,188,419 B2 | 1/2019 | Wilson et al. |
| 10,231,613 B2 | 3/2019 | Wilson et al. |
| 10,292,807 B2 | 5/2019 | Wilson et al. |
| 10,603,018 B2 | 3/2020 | Wilson et al. |
| 10,646,247 B2 | 5/2020 | Wilson et al. |
| 10,758,335 B2 | 9/2020 | Wilson et al. |
| 10,874,413 B2 | 12/2020 | Wilson et al. |
| 11,330,975 B2 | 5/2022 | Wilson et al. |
| 2001/0041899 A1 | 11/2001 | Foster |
| 2001/0047165 A1 | 11/2001 | Makower et al. |
| 2002/0029052 A1 | 3/2002 | Evans et al. |
| 2002/0072706 A1 | 6/2002 | Hiblar et al. |
| 2002/0091362 A1 | 7/2002 | Maginot et al. |
| 2002/0103459 A1 | 8/2002 | Sparks et al. |
| 2002/0148475 A1 | 10/2002 | Johnson et al. |
| 2003/0125663 A1 | 7/2003 | Coleman et al. |
| 2003/0144670 A1 | 7/2003 | Pavcnik et al. |
| 2004/0158143 A1 | 8/2004 | Flaherty et al. |
| 2004/0167558 A1 | 8/2004 | Igo et al. |
| 2004/0215339 A1 | 10/2004 | Drasler et al. |
| 2005/0014995 A1 | 1/2005 | Amundson et al. |
| 2005/0075665 A1 | 4/2005 | Brenzel et al. |
| 2005/0165466 A1 | 7/2005 | Morris et al. |
| 2005/0273159 A1 | 12/2005 | Opie |
| 2006/0094929 A1 | 5/2006 | Tronnes et al. |
| 2006/0136045 A1 | 6/2006 | Flagle et al. |
| 2006/0156875 A1 | 7/2006 | McRury et al. |
| 2006/0178646 A1 | 8/2006 | Harris et al. |
| 2006/0184187 A1 | 8/2006 | Surti |
| 2006/0235449 A1 | 10/2006 | Schubart et al. |
| 2006/0271090 A1 | 11/2006 | Shaked et al. |
| 2007/0005093 A1 | 1/2007 | Cox et al. |
| 2007/0093780 A1 | 4/2007 | Kugler et al. |
| 2007/0093781 A1 | 4/2007 | Kugler et al. |
| 2007/0123821 A1 | 5/2007 | Wang et al. |
| 2007/0129628 A1 | 6/2007 | Hirsh |
| 2007/0208368 A1 | 9/2007 | Katoh et al. |
| 2008/0033467 A1 | 2/2008 | Miyamoto et al. |
| 2008/0103480 A1 | 5/2008 | Bosel et al. |
| 2008/0228171 A1 | 9/2008 | Kugler et al. |
| 2008/0228211 A1 | 9/2008 | Gonon |
| 2008/0243065 A1 | 10/2008 | Rottenberg et al. |
| 2008/0255595 A1 | 10/2008 | Buchbinder et al. |
| 2009/0005793 A1 | 1/2009 | Pantages et al. |
| 2009/0112059 A1 | 4/2009 | Nobis |
| 2009/0149739 A9 | 6/2009 | Maschke |
| 2009/0149805 A1 | 6/2009 | Coleman et al. |
| 2009/0182192 A1 | 7/2009 | Shiono et al. |
| 2009/0209910 A1 | 8/2009 | Kugler et al. |
| 2009/0254051 A1 | 10/2009 | Von et al. |
| 2009/0270799 A1 | 10/2009 | Seto et al. |
| 2010/0076476 A1 | 3/2010 | To et al. |
| 2010/0152682 A1 | 6/2010 | Mauch et al. |
| 2010/0152843 A1 | 6/2010 | Mauch et al. |
| 2010/0241147 A1 | 9/2010 | Maschke |
| 2010/0256599 A1 | 10/2010 | Kassab et al. |
| 2011/0238038 A1 | 9/2011 | Sefi et al. |
| 2011/0264125 A1 | 10/2011 | Wilson et al. |
| 2011/0264127 A1 | 10/2011 | Mauch et al. |
| 2011/0264128 A1 | 10/2011 | Mauch et al. |
| 2012/0143234 A1 | 6/2012 | Wilson et al. |
| 2012/0289987 A1 | 11/2012 | Wilson et al. |
| 2013/0066346 A1 | 3/2013 | Pigott et al. |
| 2013/0103070 A1 | 4/2013 | Kugler et al. |
| 2013/0116715 A1 | 5/2013 | Weber |
| 2013/0172883 A1 | 7/2013 | Lopes et al. |
| 2013/0216114 A1 | 8/2013 | Courtney et al. |
| 2013/0317534 A1 | 11/2013 | Zhou et al. |
| 2014/0012301 A1 | 1/2014 | Wilson et al. |

(56) References Cited

U.S. PATENT DOCUMENTS

| | | | |
|---|---|---|---|
| 2015/0057566 A1 | 2/2015 | Vetter et al. | |
| 2015/0094532 A1* | 4/2015 | Wilson | A61B 17/12136 600/104 |
| 2015/0112188 A1 | 4/2015 | Stigall et al. | |
| 2015/0265263 A1* | 9/2015 | Wilson | A61B 8/4494 600/424 |
| 2015/0342631 A1 | 12/2015 | Wilson et al. | |
| 2015/0359630 A1 | 12/2015 | Wilson et al. | |
| 2016/0081656 A1* | 3/2016 | Abraham | A61B 8/582 600/439 |
| 2016/0166243 A1 | 6/2016 | Wilson et al. | |
| 2016/0235428 A1 | 8/2016 | Wilson et al. | |
| 2017/0035450 A1 | 2/2017 | Fletcher et al. | |
| 2017/0035455 A1 | 2/2017 | Fletcher et al. | |
| 2018/0000509 A1 | 1/2018 | Wilson et al. | |
| 2018/0214173 A1 | 8/2018 | Wilson et al. | |
| 2018/0289441 A1 | 10/2018 | Wilson et al. | |
| 2018/0333166 A1 | 11/2018 | Wilson et al. | |
| 2018/0361118 A1 | 12/2018 | Cully et al. | |
| 2019/0314620 A1 | 10/2019 | Chang et al. | |
| 2020/0275975 A1 | 9/2020 | Chen | |
| 2024/0156491 A1 | 5/2024 | Wilson et al. | |

FOREIGN PATENT DOCUMENTS

| | | | |
|---|---|---|---|
| CN | 1907243 | A | 2/2007 |
| CN | 1957861 | A | 5/2007 |
| EP | 1323448 | A2 | 7/2003 |
| JP | 2002-514111 | A | 5/2002 |
| JP | 2003033357 | A | 2/2003 |
| JP | 2003267160 | A | 9/2003 |
| JP | 2009165822 | A | 7/2009 |
| JP | 2009183516 | A | 8/2009 |
| JP | 2010509994 | A | 4/2010 |
| RU | 2108751 | C1 | 4/1998 |
| RU | 2160057 | C2 | 12/2000 |
| WO | 99000059 | A1 | 1/1999 |
| WO | 2007/005535 | A1 | 1/2007 |
| WO | 2008/063621 | A2 | 5/2008 |
| WO | 2010074853 | A1 | 7/2010 |
| WO | 2011106735 | A1 | 9/2011 |
| WO | 2012/030587 | A1 | 3/2012 |
| WO | 2012145444 | A2 | 10/2012 |
| WO | 2013119849 | A1 | 8/2013 |
| WO | 2013/159066 | A1 | 10/2013 |
| WO | 2014/110460 | A1 | 7/2014 |
| WO | 2015077515 | A1 | 5/2015 |
| WO | 2015/148581 | A1 | 10/2015 |
| WO | 2016025733 | A1 | 2/2016 |
| WO | 2017210656 | A1 | 12/2017 |

OTHER PUBLICATIONS

International Search Report and Written Opinion mailed Oct. 12, 2021 for International Patent Application No. PCT/US2021/038582, 16 pages.

Lugli, M., et al., Neovalve construction in the deep venous incompetence. J. Vasc. Surg., Jan. 2009, 49(1), 156-62.

Maleti, O., Neovalve construction in postthrombotic syndrome. Journal of Vascular Surgery, vol. 34, No. 4, 6 pages.

Decision to grant received for European Application No. 13747210.6, mailed on Sep. 19, 2019, 2 pages.

Decision to grant received for European Application No. 15718013.4, mailed on May 11, 2018, 2 pages.

Decision to grant received for European Application No. 17739356.8, mailed on Jun. 30, 2022, 2 pages.

Decision to grant received for European Application No. 19192408.3, mailed on Jul. 14, 2022, 2 pages.

Extended European Search Report dated Jul. 6, 2015 for European Appln. No. 13747210.6, 7 pages.

Extended European Search Report mailed Jan. 9, 2023 for European Appln. No. 22186576.9, 9 pages.

Extended European Search Report received for European Application No. 19192408.3, mailed on Feb. 17, 2020, 7 pages.

Final Office Action for U.S. Appl. No. 13/035,752, dated Apr. 4, 2013, 12 pages.

Final Office Action for U.S. Appl. No. 14/667,670, mailed Dec. 2, 2015, 12 pages.

Foreign Office Action dated Apr. 26, 2018 for European Appln. No. 13747210.6, 5 pages.

Foreign Office Action dated Jul. 7, 2020 for EP Patent Application No. 17739356.8; 5 pages.

Foreign Office Action dated May 28, 2021 for AU Patent Application No. 2017272363, 3 pages.

Foreign Office Action dated Nov. 20, 2019 for EP Patent Application No. 17739356.8; 6 pages.

Intention to grant received for European Application No. 13747210.6, mailed on Apr. 26, 2019, 6 pages.

Intention to grant received for European Application No. 15718013.4, mailed on Dec. 11, 2017, 6 pages.

Intention to grant received for European Application No. 17739356.8, mailed on Feb. 7, 2022, 6 pages.

Intention to grant received for European Application No. 19192408.3, mailed on Feb. 23, 2022, 6 pages.

International Preliminary Report on Patentability received for PCT application No. PCT/US13/25196, mailed on Aug. 21, 2014, 6 pages.

International Preliminary Report on Patentability received for PCT application No. PCT/US15/22344, mailed on Oct. 6, 2016, 7 pages.

International Preliminary Report on Patentability received for PCT application No. PCT/US17/35851, mailed on Dec. 13, 2018, 10 pages.

International Preliminary Report on Patentability received for PCT Patent Application No. PCT/US21/38582, mailed on Jan. 5, 2023, 9 pages.

International Search Report & Written Opinion for International Application No. PCT/US12/34138 dated Aug. 10, 2012, 8 pages.

International Search Report and Written Opinion dated Sep. 28, 2017; International Application No. PCT/US2017/035851; 32 pages.

International Search Report and Written Opinion for International App. No. PCT/US2011/026370, Dated Jul. 7, 2011, 10 pages.

International Search Report and Written Opinion for International App. No. PCT/US2013/025196, Mailed Apr. 25, 2013, 7 pages.

International Search Report and Written Opinion for International App. No. PCT/US2015/022344, mailed Jun. 11, 2015, 10 pages.

International Search Report for International App. No. PCT/US14/01 1169, dated May 22, 2014, 2 pages.

Non Final Office Action for U.S. Appl. No. 14/667,670, mailed Sep. 17, 2015, 9 pages.

Non-Final Office Action for U.S. Appl. No. 13/035,818 dated Sep. 14, 2012, 7 pages.

Non-Final Office Action for U.S. Appl. No. 13/450,432, Mailed Feb. 19, 2014, 8 pages.

Non-Final Office Action for U.S. Appl. No. 13/035,752, Mailed May 19, 2014, 11 pages.

Non-Final Office Action for U.S. Appl. No. 13/035,752, Mailed Oct. 16, 2012, 13 pages.

Notice of Allowance for U.S. Appl. No. 13/035,818, dated Feb. 22, 2013, 7 pages.

Office Action received for European Application No. 15718013.4, mailed on Jun. 29, 2017, 3 pages.

* cited by examiner

ENDOVASCULAR VALVE FORMATION SYSTEM WITH IMAGING CAPABILITY

CROSS-REFERENCE TO RELATED APPLICATIONS

This application is a continuation of U.S. patent application Ser. No. 17/355,459, filed on Jun. 23, 2021, which claims priority to U.S. Provisional Patent Application No. 63/043,087, filed on Jun. 23, 2020, the disclosures of which are incorporated herein by reference in their entireties.

TECHNICAL FIELD

The present technology generally relates to intravascular catheter systems, and more particularly to endovascular valve formation devices, systems, and methods with imaging capabilities.

BACKGROUND

Veins are blood vessels in the body through which blood flows from body structures back to the heart. Most veins include valves to facilitate blood flow towards the heart, which is especially important when the flow is against gravity. Venous reflux is a medical condition affecting the circulation of blood in veins, such as in the lower extremities, and is typically due to failure of the venous valves to function properly. As a result, blood pools in the lower extremities, causing venous hypertension, which lead in turn to unwanted clinical problems such as leg swelling, pain, and ulceration. Venous reflux can occur in both superficial veins (veins closer to the skin) and deep veins. Because deep veins can be difficult to access, deep veins are also more difficult to treat.

Existing methods for treating damaged or diseased valves in deep veins include surgical repair or replacement of the diseased valve, or vessel bypass around the diseased vein segment. However, these surgical treatment options include relatively lengthy recovery times and expose the patient to the risks involved in any vascular surgical procedure, such as infection and clotting. Experimental treatments, such as implantable venous valves, external venous valve banding, and heat-induced vein shrinkage, have been attempted but each treatment has experienced significant shortcomings. Compression stockings are sometimes used to ameliorate symptoms but do not address the underlying problem of dysfunctional venous valves.

Imaging technologies, such as ultrasound imaging, are often used with endovascular procedures to help guide and assess the procedure. Intravascular ultrasound ("IVUS") systems have two main components: an intravascular catheter with one or more ultrasound transducers at the distal end, and an imaging control and display console. The catheter is typically positioned in the area of interest over a guidewire, for example an 0.014" or 0.018" diameter guide wire. An electrical connection is made between the ultrasound imaging catheter and the imaging console to transmit signals from the transducer in the catheter to the console, typically with a cable that attaches to the catheter on one end and the imaging console on the other. The cable often includes a catheter control unit on the catheter connection side. The imaging console receives the signals and recreates an ultrasound image of the vessel, which is displayed on a screen on the console. Recordings, measurements, and variable imaging views may all be obtained using controls on the console. Examples of existing IVUS technology include the Opticross Intravascular Ultrasound Catheter and corresponding Polaris Guidance System (Boston Scientific Corporation) and the Eagle Eye Ultrasound Catheter and corresponding Core Console (Koninklijke Philips N.V.). The Boston Scientific IVUS system uses rotational transducer technology, in which a single transducer is mounted on a drive shaft within the catheter and rotated to obtain a 360° view of the vessel wall. The Philips IVUS system uses phased array technology, in which multiple transducers are arranged around a central core and the signals are integrated to create the 360° view of the vessel wall.

Other intravascular imaging technologies include optical coherence tomography (OCT), which similarly comprises a catheter component and a control and display console, and angioscopy. In contrast to IVUS, OCT uses light waves rather than ultrasound signals to obtain intravascular images. Angioscopic technologies use a catheter with light fibers to deliver light to the distal end of the catheter and transmit an image from the distal end to a camera connected to the proximal end of the catheter. Current angioscopic systems require a clear fluid path to visualize the vessel wall.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure. Reference numbers/indicators used consistently throughout the drawings and description for ease to refer to items having similar structure, features, and/or functions. Identical reference numbers/indicators are not indicative that the items are identical.

DETAILED DESCRIPTION

Figure 1:
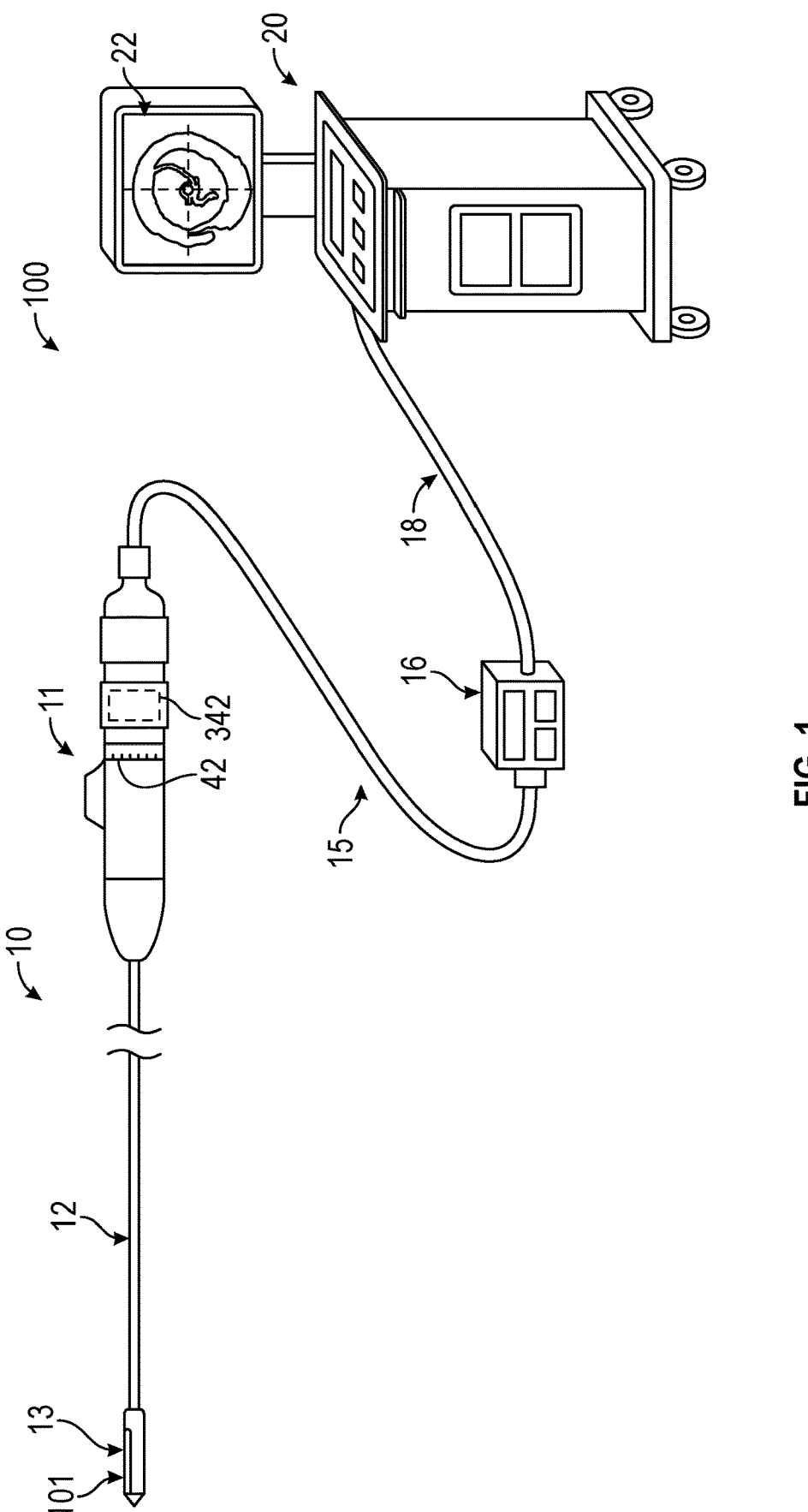
FIG. 1 illustrates a valve creation and imaging system including an imaging console configured in accordance with embodiments of the present technology.

The present technology relates generally to medical systems, devices and methods for tissue manipulation and the creation of autologous tissue valves within the vessel wall of a subject (e.g., a human patient) while imaging the vessel and/or vessel wall before, during, and/or after valve creation. The valve formation and imaging systems disclosed herein can include imaging means that are particularly suited for use with devices and methods for accessing vessel wall and forming autologous valves. In some embodiments, the imaging components are coupled with and/or embedded in the valve creation device such that the two can be used optimally in tandem. Various embodiments of the present technology also include means for communicating positional information related to one or more imaging transducers in relation to the valve creation device and/or specific components thereof to facilitate image interpretation during valve creation procedures. Specific details of several embodiments of the technology are described below with reference to FIGS. 1-16. Although many of the embodiments are described below with respect to valve creation devices, systems, and methods for creating autologous valves in veins, other applications and other embodiments in addition to those described herein are within the scope of the technology. For example, the present technology may be used to create autologous valves at other target sites (e.g., in arteries or cardiac structures) and/or for cutting tissue (e.g., separating tissue layers, cutting tissue flaps) for reasons other than valve creation. Additionally, several other embodiments of the technology can have different configurations, components, or procedures than those described herein, and features of the embodiments shown can be combined with one another. A person of ordinary skill in the art, therefore, will understand that the technology can have other embodiments with additional elements, or the technology can have other embodiments without several of the features shown and described below with reference to FIGS. 1-16.

With regard to the terms "distal" and "proximal" within this description, unless otherwise specified, the terms can reference a relative position of the portions of an endovascular device and/or an associated delivery system with reference to an operator (e.g., a clinician, robotic device). For example, in referring to a catheter suitable to deliver a valve creation means and/or an imaging means within a blood vessel, "proximal" can refer to a position closer to the operator of the device or an incision into the vessel wall, and "distal" can refer to a position that is more distant from the operator of the device or further from the access site into the vessel wall (e.g., the end of the catheter).

Systems configured in accordance with some embodiments of the present technology can include a valve creation device and a means for visualizing the vessel walls. The valve creation device can include a handle assembly and an elongated tubular member (e.g., a catheter, shaft, tube) having a proximal end attached to the handle assembly and a distal end having an end effector assembly configured to access a vessel wall layer (between the inner and outer boundaries of the vessel wall). The elongated tubular member can be configured (e.g., sized, shaped, arranged, and/or positioned) for insertion into a vessel (e.g., a vein) of a patient, and the end effector assembly can be configured (e.g., sized, shaped, arranged, and/or positioned) to gain access to the layers of the vessel wall and create an autologous tissue valve. In some embodiments, the valve creation devices and systems can include various features generally similar to the devices, systems, and methods for accessing vessel wall layers, cutting vessel tissue, and forming new autologous disclosed in International Patent Application No. PCT/US2011/026370, filed Feb. 25, 2011; International Patent Application No. PCT/US2012/034138, filed Apr. 18, 2012; International Patent Application No. PCT/US2013/025196, filed Feb. 7, 2013; International Patent Application No. PCT/US2015/022344, filed Mar. 24, 2015; International Patent Application No. PCT/US2015/066205, filed Dec. 16, 2015; U.S. patent application Ser. No. 15/478,143; and International Patent Application No. PCT/US2017/035851, filed Jun. 2, 2017; each of which is incorporated herein by reference in its entirety.

The visualization means can include one or more components integrated into and/or coupled with components of the valve creation means (e.g., the distal end effector assembly), and/or the visualization means can comprise separate catheters that are selectively coupled together with one or more components of the valve creation means. In some embodiments, for example, the visualization means is mechanically and/or electronically coupled to the valve creation means. The electronic coupling can be provided by, for example, position sensors, control systems, information feedback systems for the user, and/or other electronic sensors or systems for associating the visualization and valve creation means together. In some embodiments, the visualization means includes an intravascular imaging catheter which may function either independently or in conjunction with the valve creation means and which contains features that are particularly suited for imaging with the end effector assembly to guide one or more steps of a valve formation procedure. Although the visualization means is discussed primarily herein as an ultrasound imaging transducer, one of skill in the art will understand that the visualization means can be any other suitable element movable and/or affixed according to the embodiments described below. For example, the imaging element can be any other suitable ultrasound imaging element, an optical coherence tomography element, or any other suitable imaging element. The headings provided herein are for convenience only and should not be construed as limiting the subject matter disclosed.

Selected Embodiments of Valve Creation Devices with Integrated IVUS

FIG. 1 illustrates a tissue manipulation and imaging system 100 (also referred to as "the system 100" and/or "the valve creation and imaging system 100") including a valve formation device 10 (also referred to as "the device 10," "the vessel wall access device," and/or "the valve creation device 10") and an imaging console 20 (also referred to as "the console 20") configured in accordance with embodiments of the present technology. The device 10 can include a handle assembly 11 (also referred to as the "handle 11"), a catheter shaft 12 (also referred to as an "elongated shaft" or "catheter"), and an end effector assembly 101 (also referred to as a "valve creation assembly 101") at a distal end portion 13 of the catheter shaft 12. The device 10 includes means for accessing the tissue wall layers of a vessel and means for forming a valve by dissecting, cutting, and/or otherwise manipulating the tissue wall layers to create a valve pocket.

The device 10 can further include a means for imaging tissue on the distal end portion 13. As described in further detail below, the imaging means can include one or more imaging components (e.g., transducers) to provide intravascular imaging via ultrasound, optical coherence tomography, and/or other suitable imaging mechanisms. The handle 11 can include or be coupled to a first cable 15 (also referred to as the "connector cable 15"), which in turn is connected to a catheter control unit 16, a second cable 18, and finally to the imaging console 20. The imaging means on the distal end portion 13 can be connected electrically, e.g., via wires (not shown), extending from the imaging means to the imaging console 20. For example, the wires can extend through the catheter shaft 12, the handle 11, the connector cable 15, the control unit 16, and the second cable 18 to the console 20. Images collected from the imaging means at the distal end portion 13 are displayed on a display 22 (e.g., a screen or monitor) of the console 20, and serve to guide a valve creation or other intravascular procedure. Variations of this configuration may be used to connect the imaging means integrated with the device 10 to imaging console 20 to enable the same or similar functions.

Figure 2:
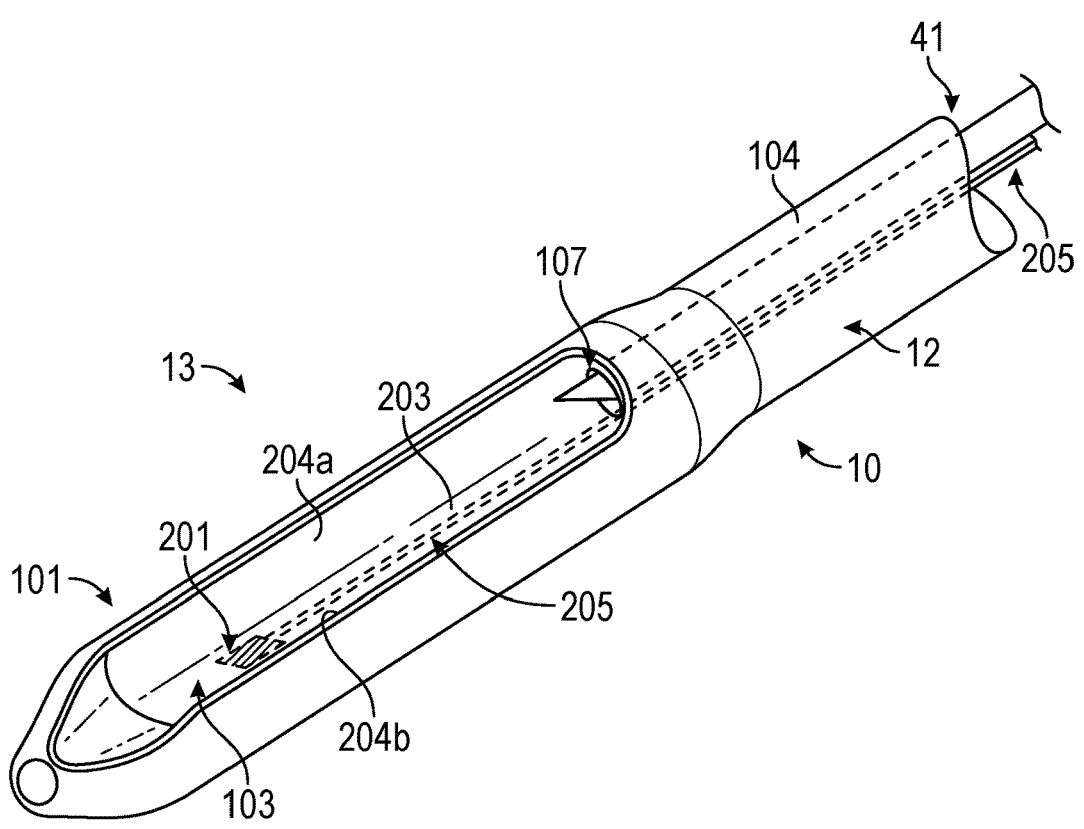
FIG. 2 is an isometric view of a distal portion of a valve creation device with integrated imaging transducers configured in accordance with embodiments of the present technology.

FIG. 2 is an isometric view of the distal end portion 13 of the valve creation device 10 of a valve creation and imaging system (e.g., the system 100 of FIG. 1) in accordance with embodiments of the present technology. The device 10 can include an imaging transducer 201 (also referred to as "transducer 201") affixed to a position at distal end portion 13, such as to a portion of the end effector assembly 101. The transducer 201 may comprise one or more ultrasound transducer elements. As described above, stand-alone IVUS catheters either rotate a single transducer chip or employ multiple transducer chips arrayed around a central shaft to obtain a 360° view of a vessel. In some embodiments, operation of the device 10 provides a section of vessel wall in which a valve is to be formed, and therefore the device 10 does not include a fully rotational chip or multiple chips arrayed completely around the IVUS catheter shaft may not be needed. In these embodiments, the device 10 can include one or more transducer chips that obtain a field of view sufficient to provide imaging information to help guide the user before, during, and/or after a valve creation procedure. In other embodiments, the transducer 201 may provide a fully circumferential (i.e., 360°) view of the vessel and include one or more fully rotational transducer chips or a plurality of chips arrayed around a central core. In any of these embodiments, the term "transducer" may refer to one or more transducer chips which, in composite, comprise a transducer. The transducer 201 can be an ultrasound imaging transducer, similar in frequency and resolution to those used in intravascular ultrasound (IVUS) catheters. For example, the transducer frequency may be between 20 and 70 MHz. As further shown in FIG. 2, the transducer 201 can be electrically coupled to electrical wires 205 (also referred to as "electrical connectors") that travel down the catheter shaft 12 and couple with the connector cable 15 (FIG. 1) and, eventually, the imaging console 20 (FIG. 1).

As shown in FIG. 2, the transducer 201 can be affixed (e.g., embedded, mounted) within a trough section 103 (also referred to as a recessed section) of the end effector assembly 101. The trough section 103 can include sidewalls 204 (identified as a first sidewall 204a and a second sidewall 204b) extending from and spaced apart from each other by a base wall 203 (or "base surface 203") to define a hollow space or region, open to the surrounding environment (e.g., the vessel, blood flow), and a proximal opening 107 (also referred to as "the proximal port 107") of a device lumen 104 (also referred to as a "first lumen 104" and a "first catheter lumen 104") of the catheter shaft 12 can be positioned proximal to, at the proximal edge of, or within a proximal region of the trough section 103. This arrangement of the proximal port 107 and the open trough section 103 allows devices (e.g., needles, cutting elements, tubes, sensors, expanders) to move partially or completely therein as they project distally beyond the proximal port 107, thereby allowing the components to interact with surrounding structures (e.g., the vessel walls, other tissue). In the illustrated embodiment, the transducer 201 is positioned on or within the base wall 203 of the trough section 103 such that devices can extend over the transducer 201 when projecting distally beyond the proximal port 107 to allow for visualization of the device during movement. For example, a tissue separation and/or cutting mechanism can extend over the transducer 201 during a value formation procedure, and the transducer 201 can image the valve dissection (e.g., imaging components of the device 10 and/or the vessel wall) during the procedure. In various embodiments, the transducer 201 is positioned elsewhere along the distal end portion 13 of the device 10, such as on an exterior sidewall of the end effector assembly 101, along the catheter body proximal to the end effector assembly 101, and/or along tissue cutting elements. In some embodiments, the device 10 may include a plurality of transducers 201 fixedly attached (e.g., embedded, adhesively joined, otherwise affixed) to various different positions of the distal end portion 13 of the device 10 to provide various different views at different positions during intravascular procedures, for example as discussed below with respect to FIG. 4.

Figure 3:
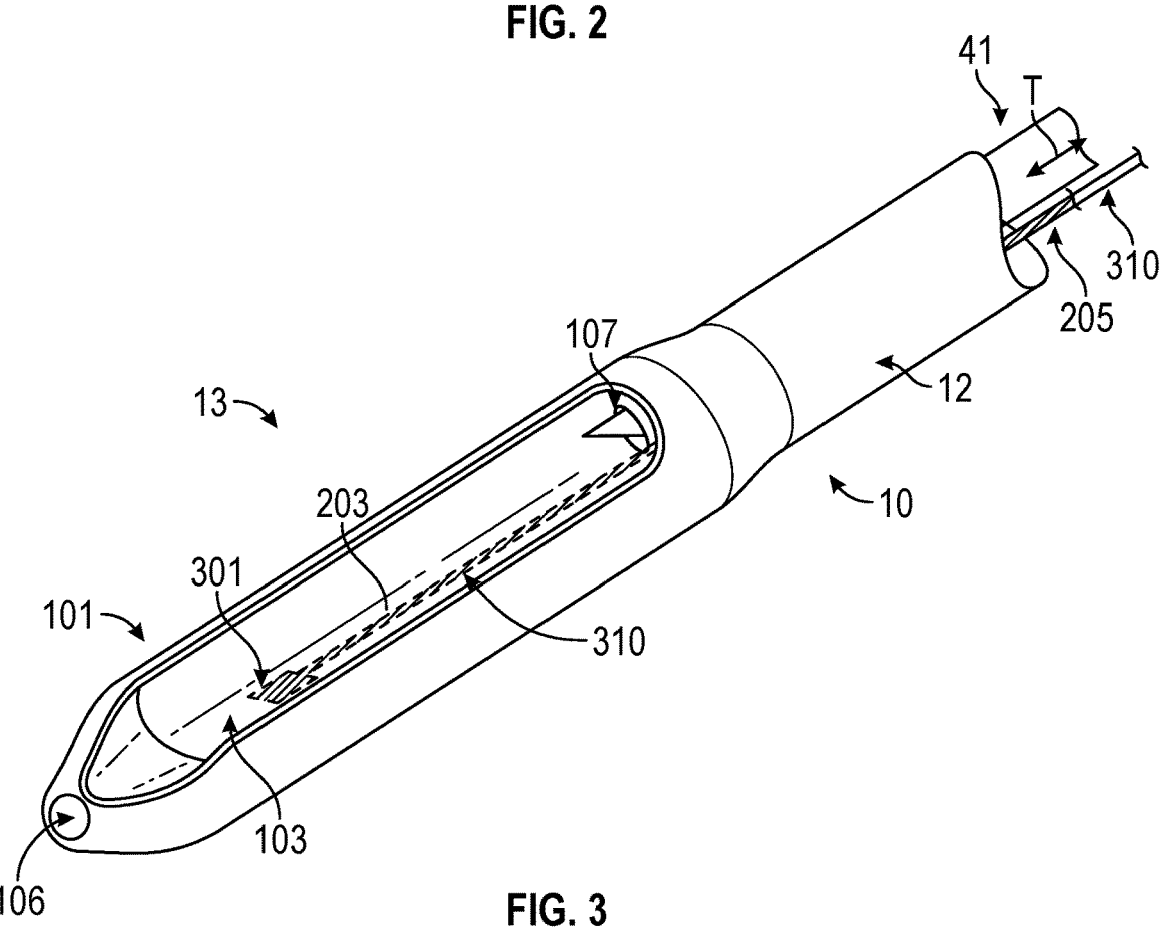
FIG. 3 is an isometric view of a distal portion of a valve creation device including a movable transducer configured in accordance with embodiments of the present technology.

FIG. 3 is an isometric view of the distal end portion 13 of the valve creation device 10 including a movable transducer 301 configured in accordance with embodiments of the present technology. In the illustrated embodiment, the transducer 301 is movable within and/or along the distal end portion 13 of the shaft 12, such as along a length of the end effector assembly 101. As shown in FIG. 3, the transducer 301 can be connected to a movable component 310 (e.g., a hypotube or transducer shaft, also referred to as "the transducer shaft 310") that extends to or is otherwise operably coupled to the handle assembly 11 (FIG. 1). The wires 205 connecting the transducer 301 to the connector cable 15 can travel along or through the transducer shaft 310. An actuator 17 (FIG. 1) of the handle assembly 11 can control the movement and position of the transducer 301 with respect to the distal end portion 13 by translating the transducer shaft 310 forwards or backwards (proximally and distally), as indicated by double-ended arrow T. In some embodiments, the transducer 301 can additionally, or alternatively, be rotated about an axis parallel with the catheter shaft 12. In some such embodiments, the actuator (FIG. 1) of the handle assembly 11 can control the rotation of the transducer 301 by actuating the movable component 310. In some embodiments, the actuator 17 (FIG. 1) can be positioned elsewhere on the device 10 or part of a separate control element operably coupled to the transducer 301.

Referring to FIGS. 1 and 3 together, the handle assembly 11 includes markings or indicators 44 to relay the position of the transducer 301 to the user. In some embodiments, the transducer shaft 310 is operably coupled to an indicator (e.g., position markings, an electronic display) that is visible on an external surface of the handle assembly 11. In some embodiments, the transducer shaft 310 is coupled to a position sensor 342 in the handle assembly 11. In some embodiments, the position sensor 342 can transmit position information associated with the transducer 301 together with the imaging data to the imaging console 20 (FIG. 1) for display on the display 22 (FIG. 1).

In some embodiments, the transducer 301 can translate along the longitudinal axis of the catheter shaft 12 in a manner that allows the transducer 301 to be positioned at more locations along on the distal end portion 13. In these and other embodiments, the transducer 301 is configured to move such that the transducer 301 extends distally beyond the distal terminus of the distal end portion 13 to view the vessel or other anatomical structures distal to the device 10. In this and other embodiments in which the transducer 301 extends outside of the device 10, the transducer 301 may include a protective outer shell (e.g., a tube extending over the transducer itself), a coating, and/or encapsulation.

In the embodiment illustrated in FIG. 3, the transducer 301 and the transducer shaft 310 extend through and move within a second catheter lumen 106 separate from the first catheter lumen 104. The second catheter lumen 106 can extend through at least a portion of the distal end portion such that the second catheter lumen 106 extends below the base surface 203 along the trough section 103 This positioning within an enclosed lumen along the trough section 103 allows the transducer 301 to be actuated without contacting tissue dissection components, cannula, needles, and/or other devices within the trough section 103.

In various embodiments, the transducer 301 and the transducer shaft 310 extend through the first lumen 104 and exit through the proximal port 107 such that the transducer 301 can be actuated and provide image data from various positions within the open region of the trough section 103. In these embodiments where the transducer 301 and the transducer shaft 310 extend through the first catheter lumen into the trough section 103, the second catheter lumen can be smaller, allowing only for smaller tools (e.g., a guidewire) and/or be omitted from the end effector assembly 101.

In various embodiments, the transducer 301 and the transducer shaft 310 define, at least in part, a transducer assembly that can be completely removed from the device 10 (i.e., separated, taken out of the catheter shaft 12). In some such embodiments, the luminal space used to position the moveable transducer assembly in device 10 can also be used by a guidewire and/or other member when positioning the device 10 in a target vessel to be treated. In use, the device 10 is first positioned over a guidewire, for example an 0.035" or 0.038" diameter guidewire to a desired target site within a vessel or other portion of the body. Once positioned at the target site, the guidewire can be removed and replaced with the movable transducer assembly. Unlike existing stand-alone imaging catheters, the movable transducer assembly does not itself require a lumen for a guidewire because the removable transducer assembly is delivered via the device 10, rather than in the vessel alone. Further, because the movable transducer assembly can share the luminal space with the guidewire via sequential delivery, the movable transducer assembly may not increase size of the catheter shaft 12 and/or the end effector assembly 101.

In some embodiments, the transducer 301 includes a transducer array that provides for 360° visualization of a vessel wall or may include a transducer array that only images a section of the vessel wall (e.g., a 180° section, a 90° section, a 60° section, a 45° section, a section smaller than 45°, a section greater than 180°, and/or anywhere therebetween). When the transducer 301 provides a smaller, sectional view (e.g., less than) 360°, the movable transducer assembly may have a smaller outer dimension (e.g., diameter) than stand-alone imaging catheters. This outer dimension is further reduced by the omission of the guidewire lumen. As a result, the movable transducer assembly and the device 10 can each have a lower profile.

The movable transducer assembly can also include features at a proximal end portion of the transducer shaft 310 that interface with position control actuators (e.g., along the handle assembly 11 (FIG. 1), or in a separate transducer controller) to control the position of the transducer 301. Additionally, or alternatively, the movable transducer assembly can include features at the proximal end portion that interface with a position indicator and/or position sensors 342 in the handle assembly 11 as described above, or in a separate transducer controller.

Figure 4:
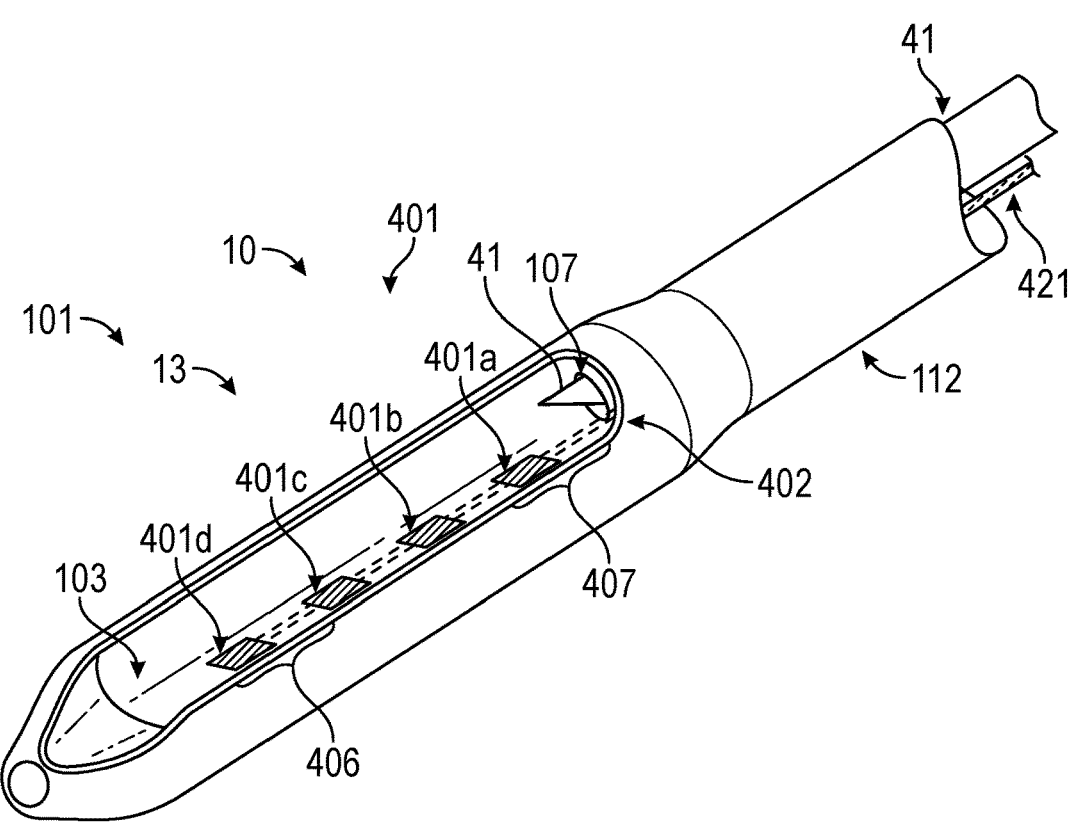
FIG. 4 is an isometric view of a valve creation device including multiple transducers affixed to a distal end portion of the device in accordance with embodiments of the present technology.

FIG. 4 is an isometric view of the distal end portion 13 of the valve creation device 10 including multiple transducers (referred to individually as first through fourth transducers 401a-401d, respectively, and collectively as transducers 401) affixed to the end effector assembly 101 in accordance with embodiments of the present technology. The transducers 401 are spaced apart along the length of the end effector assembly 101 and/or face multiple directions from one or more positions along the end effector assembly 101. The console 20 (FIG. 1) can be configured to show images from the multiple transducers 401, either simultaneously in two or more windows or serially at different stages in the procedure. In the illustrated embodiment, there are four transducers 401a, 401b, 401c and 401d spread out over the length of the end effector assembly 101. In the illustrated embodiment, the four transducers 401 are fixed in position, thereby providing certainty about where the image data from each transducers 401 is being obtained. In some embodiments, the first transducer 401a (e.g., the proximal-most transducer) is positioned near or at the location 402 along the distal end portion 13 where a puncture device may access tissue (e.g., the wall of the vessel). For example, in the illustrated embodiment the first transducer 401a is near or close to alignment with the exit port 107. The fourth transducer 401d (e.g., the distalmost transducer) can be positioned at a distal location 406 (or "distal point 406") along the trough section 103 that is near or generally aligns with the distalmost location of expected access into the vessel wall (e.g., at the distalmost end of the end effector assembly 101 and/or at the distalmost end of the trough section 113). The intermediate transducers 401b and 401c are positioned to provide image data from intermediate positions between the first and fourth transducers 401a, 401d, such that the combination of the transducers 401 provides for imaging at specified locations along lengthwise segment of the trough section 102 and the surrounding native anatomy. Wires 405 connected to each transducer may be integrated into a multi-strand cable 421 traveling the length of catheter shaft 12 to connect each of the transducers 401 to the imaging console 20 (FIG. 1).

In some embodiments, the end effector assembly 101 includes more than four transducers 401, e.g., as many as 10 or more transducers over the length of the distal end. The number of transducers 401 is only limited by the physical dimensions of the distal end portion 13 (e.g., the length and width of the end effector assembly 101) and transducer chip technology, and thus the end effector assembly 101 can be configured to provide optimal resolution of images over the length of the distal end portion 13. In some embodiments, the end effector assembly 101 includes less transducers 401 (e.g., one transducer, two transducers, or three transducers). Further, in some embodiments, one or more of the multiple transducers 401 are movable along the end effector assembly 101. For example, the end effector assembly 101 can include the first transducer 401a fixed in place at a proximal point 407, the fourth transducer 401d fixed in place at the distal point 406, and the second transducer 202b movable between the distal point 406 and the proximal point 407. The first and fourth transducers 202a, 202d can provide image data from fixed points of interest while the second transducer 202b can be translated according to the position during the procedure and/or in conjunction with the tissue dissection components.

When using the device 10 of FIG. 4 during a valve formation procedure, the distal end portion 13 of the device 10 can be inserted into the vessel and delivered to a target site. A puncture or tissue access component 41 of the end effector assembly 101, for example a needle, is then advanced through the exit port 107. At this step, the image data from the first transducer 401a is viewed on the display 22 (FIG. 1) to view the puncture step. As the puncture element is advanced in the tissue layers, image data from successive transducers 401b and 401c are displayed on the display 22. Completion of travel of the puncture element is confirmed by the image data from the fourth transducer 401d. In this embodiment, a separate imaging catheter did not have to be inserted and positioned successively at different positions to appropriately and/or completely image the valve formation procedure. In some embodiments, the console 20 (FIG. 1) includes signal processing software which automatically displays the relevant image(s). For example, the processing software displays the image relevant to the position of the needle is displayed on the screen. In various embodiments, the processing software uses image analysis algorithms to display the image with the needle in the frame, or cycles to the next image when the needle enters the frame. In some embodiments, the console 20 (FIG. 1) includes signal processing software allowing a user to select the image displayed on the console 20. For example, a user can manually advance the displayed image to the next transducer. The advancement may be performed by the user of the device or by a second user, and/or the advancement control may be on a secondary user interface, such as a foot pedal, a button on the control unit, a button, and/or other actuator on or operably coupled to the imaging console. In some embodiments, as discussed in more detail below with respect to FIGS. 12 and 14, the device 10 can include one or more position sensors that can identify the position of one or more transducers relative to the handle assembly; the position of the tissue access component 41 and/or the tissue dissection component 42 (FIG. 1) relative to the handle assembly; and/or the position of the tissue access component 41 and/or the tissue dissection component 42 relative to the imaging transducer(s). In some such embodiments, the processing software uses the relative positions from the position sensors to display the image with the tissue access component 41 and/or the tissue dissection component 42 in the frame (or as they enter the frame).

Figure 5:
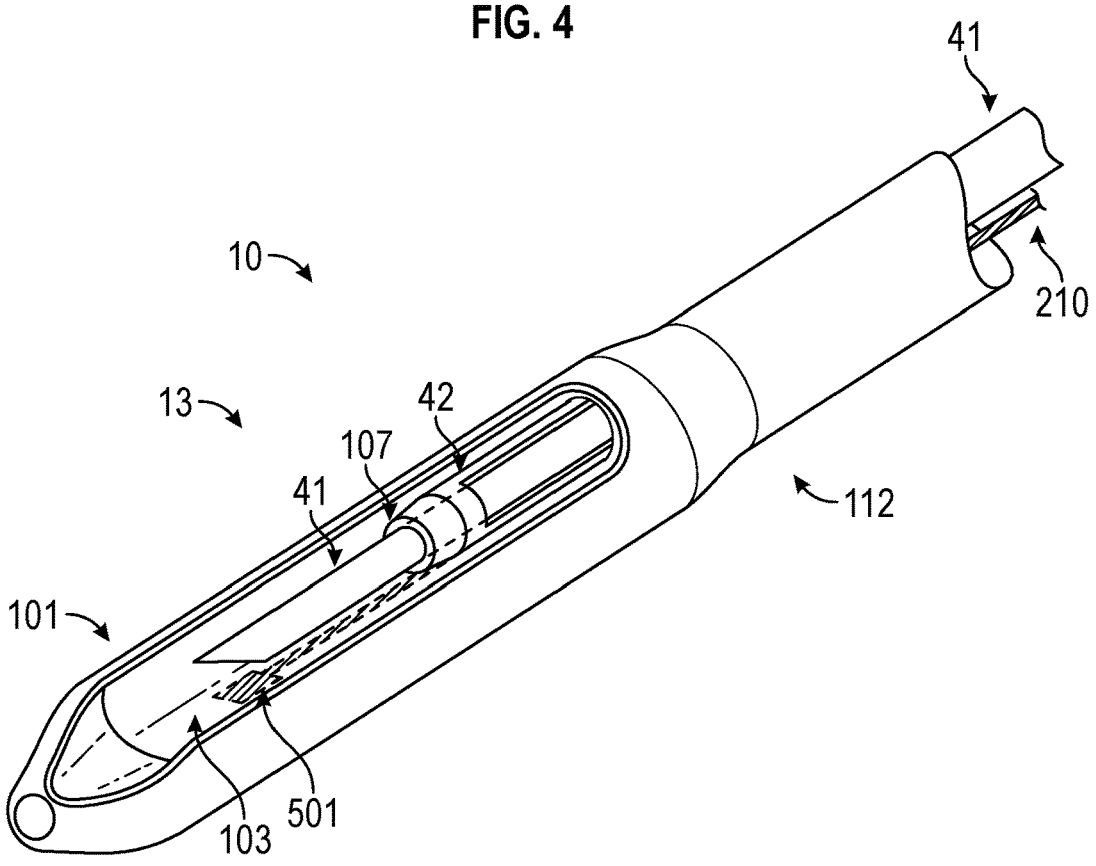
FIG. 5 is an isometric view of a distal portion of a valve creation device including an imaging transducer coupled to device components in accordance with embodiments of the present technology.

FIG. 5 is an isometric view of the end effector assembly 101 of the valve creation device 10 including a moveable imaging transducer 501 coupled to one or more components of the device 10 in accordance with embodiments of the present technology. In the illustrated embodiment, the end effector assembly 101 includes the tissue access component 41 (e.g., a needle) and a tissue dissection component 42 (e.g., an expandable mechanical structure or an expandable balloon). In some embodiments, the tissue access component 41 is slideably coupled and concentric to the tissue dissection component 42. In some such embodiments, the distal end portion 13 of the device 10 is delivered to a target location in a vessel (e.g., a vein) at an intended dissection site, and the tissue access component 41 then projects from the exit port 107 such that advancement of the tissue access component 41 punctures the vessel wall and, in certain embodiments, advances in a linear manner (generally aligned with the longitudinal axis of the distal end portion 13) between layers of the vessels wall. The tissue dissection component 42 can then advance over the tissue access component 41 into the punctured vein wall layer, and actuation of the tissue dissection component 42 can move the tissue dissection component 42 in a manner that creates a valve leaflet from a portion of the vessel wall. In some embodiments, the tissue access component 41 and the tissue dissection component 42 can be sequentially advanced to puncture and manipulate the vein wall layer. Suitable puncture elements and valve dissection devices are described in, for example, International Patent Application No. PCT/US2011/026370, filed Feb. 25, 2011; International Patent Application No. PCT/US2012/034138, filed Apr. 18, 2012; and International Patent Application No. PCT/US2013/025196, filed Feb. 7, 2013; each of which is incorporated herein by reference in its entirety.

In the illustrated embodiment, the imaging transducer 501 is moveable (e.g., in a similar manner as shown and described with respect to FIG. 3) and positionally coupled to the tissue access component 41 and/or the tissue dissection component 42. For example, the imaging transducer 501 can be operably coupled to the tissue access component 41 to advance concurrently with the tissue access component 41. In such embodiments, the imaging transducer 501 is automatically aligned with the tissue access component 41, for example at the needle tip, or a few millimeters ahead or behind the needle tip. In some embodiments, the imaging transducer 200 is alterably coupled to the tissue access component 41 and/or the tissue dissection component 42. For example, the imaging transducer 501 can be operably coupled to the tissue access component 41 while the tissue access component 41 punctures a vessel wall, then decouple from the tissue access component and be operably coupled to the tissue dissection component 42 while the tissue dissection component 42 dissects the vessel wall. Any coupling, as referred to in this context, may be a mechanical coupling between the imaging transducer 501 and one or both of the tissue access component 41 and the tissue dissection component 42.

Figure 6:
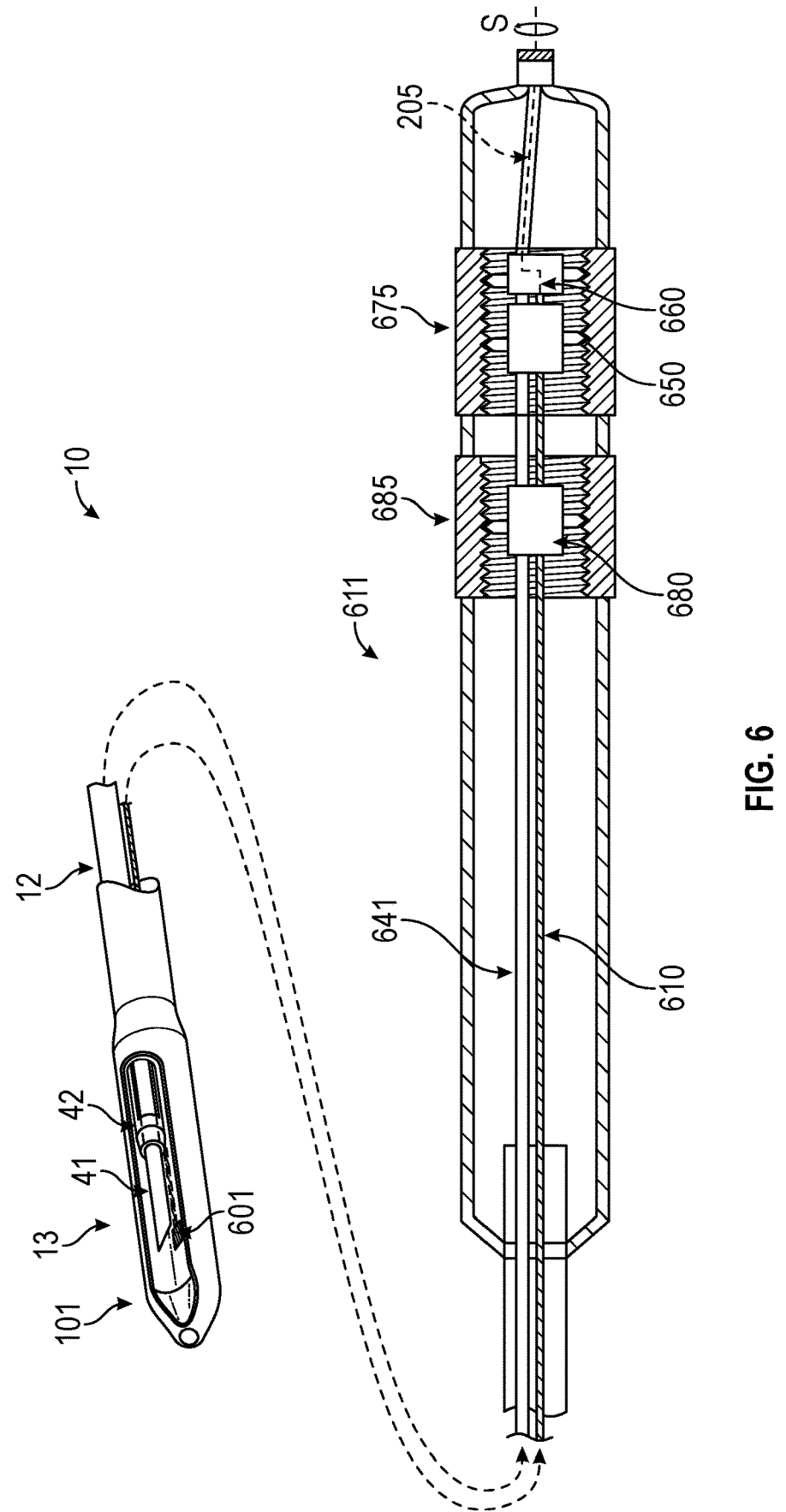
FIG. 6 illustrates a valve creation and imaging system with a cross-sectional view of a handle assembly including a mechanism for coupling an imaging transducer to a distally-positioned valve creation assembly in accordance with embodiments of the present technology.

In some embodiments, the mechanical coupling is positioned within the handle assembly 11 (FIG. 1) of device 10. FIG. 6, for example, illustrates a valve creation and imaging system 600 ("system 600") with a cross-sectional view of a handle assembly 611 configured to couple the imaging transducer 601 to one or more components of the valve creation assembly 101 in accordance with embodiments of the present technology. The system 600 can include various features and components generally similar to the system 100 of FIG. 1 and the devices of FIGS. 2-5 described above. As shown in FIG. 6, the handle assembly 611 can include a tissue access hub 650 (also referred to as a "needle hub 650") coupled to a proximal end portion of a tissue access component 641 and a transducer hub 660 (also referred to as an "imaging hub 660") coupled to a proximal end portion of a transducer shaft 610 of imaging transducer 601. A mechanism within in the handle assembly 611 couples the movement of the needle hub 650 and the transducer hub 660, thereby coupling the movement of the tissue access component 641 and the transducer 601. In the embodiment illustrated in FIG. 6, for example, a first adjustment component 675 (e.g., a wrenchable, screwable, twistable, and/or rotatable component) couples to the hubs 650 660 through grooved tracks and mating means. When the first adjustment component 675 is turned about an axis S (e.g., the longitudinal axis of the handle assembly 611), the hubs 650, 660 translate forwards or backwards along the axis S depending upon the direction of the rotation. In other embodiments, the first adjustment component 675 and/or other actuation means can be manipulated in a different manner (e.g., sliding, depressing a button, ratcheting) to advance and/or retract the needle hub 650, the imaging hub 660, and the components coupled thereto. In some embodiments, the position of the imaging hub 660 is fixed relative to the needle hub 650, thereby fixing the position of the transducer 601 relative to the tissue access component 41 (or another suitable component of the valve creation assembly 101). In various embodiments, the first adjustment component 675 can be selectively uncoupled from the needle hub 650 and/or the imaging hub 660 via one or more actuators of the handle assembly 611. In such embodiments, the user can selectively move the transducer 601 and/or the tissue access component 41 together and/or independently. The independent movement allows the user to, for example, selectively position the transducer 601 (e.g., in a similar manner as the transducer 601 described with respect to FIG. 3) to image the needle tip, other components of the valve creation assembly 101, the patient's vessel wall, and/or other parts of the patient's vein during steps of the procedure.

As further shown in FIG. 6, the handle assembly 611 can include a second adjustment component 685 carried by the handle assembly and coupled to a dissector hub 680, which is in turn coupled to a proximal end portion of the tissue dissection component 42. In some embodiments, the user can selectively couple the imaging hub 660 to the second adjustment component 685, thereby linking the position of the imaging hub 660 (and therefore the transducer 601) and the position of the dissector hub 680 (and therefore the dissector component). In some embodiments, the user can selectively couple and decouple the imaging hub 660 between the adjustment components 675, 685, thereby selectively the adjusting the link of the imaging hub 660 between the needle hub 650 (and therefore the tissue access component 41, and the dissector hub 680. In some embodiments, the user can selectively couple and decouple the hubs 650, 680 between the adjustment components 675, 685, thereby coupling and decoupling both the tissue access component 641 and the tissue dissector component 42 together and/or to decouple the imaging hub 660 from any other device component (thereby permitting the user to independently move the transducer 601). Such embodiments allow the user to move the transducer 601 together with different components of the valve creation assembly 101 and/or independently during different stages of the valve creation procedure.

Figures 7, 8, 9:
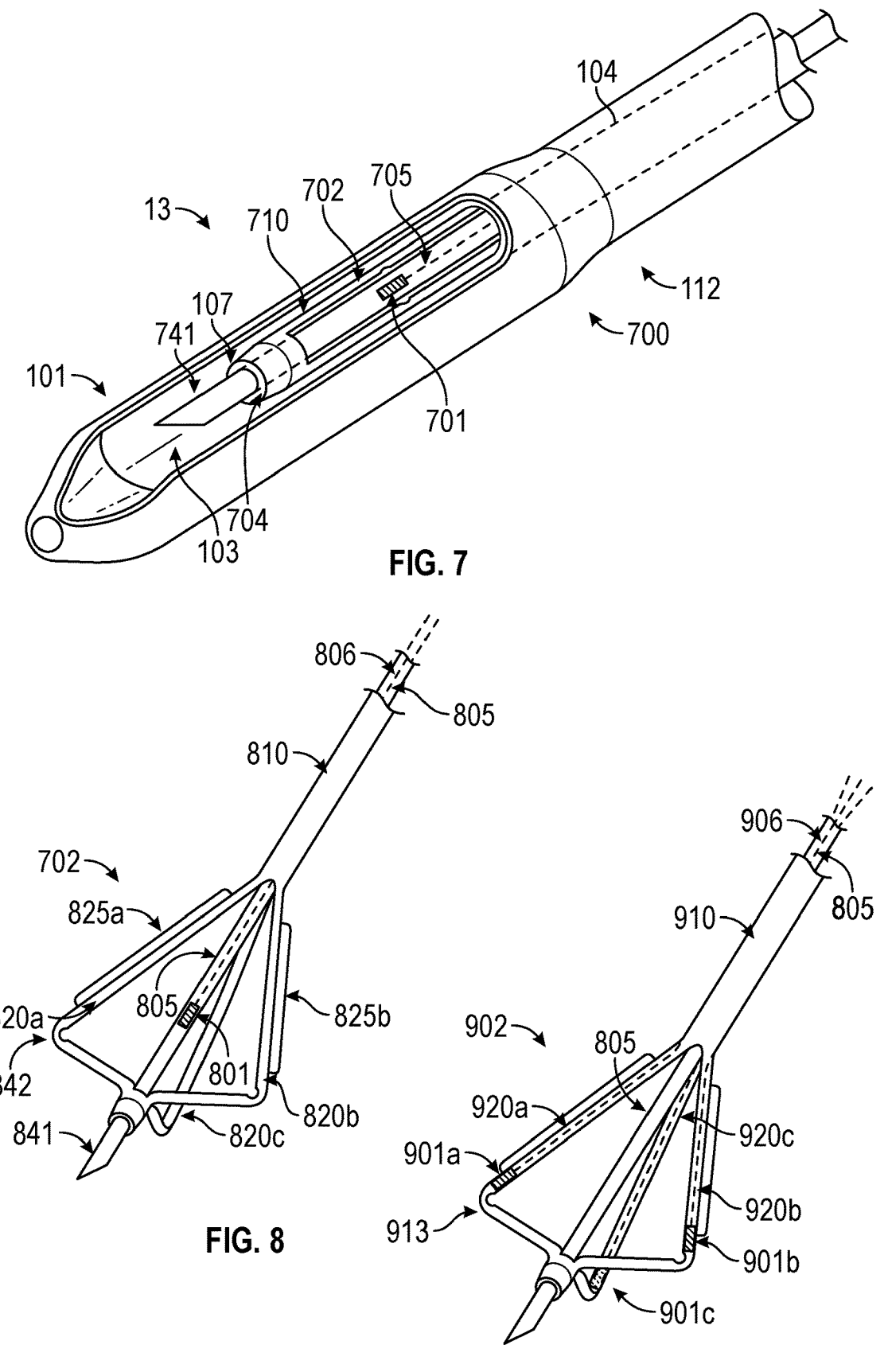
FIG. 7 is an isometric view of a distal portion of a valve creation device including a transducer is affixed to a tissue dissection component in accordance with embodiments of the present technology.
FIG. 8 is an isometric view of the tissue dissection component of FIG. 7 configured in accordance with embodiments of the present technology.
FIG. 9 is an isometric view of a distal portion of a valve creation device including a transducer affixed to a tissue dissection component in accordance with embodiments of the present technology.

In some embodiments, the imaging transducer is directly attached (e.g., via mechanical and/or adhesive connection) to a component of the valve creation assembly 101. FIG. 7, for example, is an isometric view of the distal end portion 13 of a valve creation device 700 with a fixedly attached transducer 701 configured in accordance with embodiments of the present technology. In the illustrated embodiment, the transducer 701 is affixed to a mechanically expandable tissue dissection assembly 702, any component therein. The tissue dissection assembly 702 can include an inner member 705 (e.g., a tissue access component as described with respect to FIGS. 4-6) and an expandable outer member 710 that can be used to dissect tissue (e.g., a tissue dissector component as described with respect to FIGS. 4-6). In the illustrated embodiment, the inner member 705 (e.g., the tissue access component 741 or another suitable needle) is slideably disposed inside a lumen 704 (e.g., a central lumen) extending through the outer member 710 of the tissue dissection assembly 702 such that the inner member 705 can move (e.g., translate longitudinally) relative to the tissue dissection assembly 702 along the longitudinal axis of the first lumen 104. In some embodiments, the outer member 710 can be mechanically expandable. In some embodiments, the outer member 710 can include an expellable component (e.g., an expandable balloon). As described in more detail below, the transducer 701 can be affixed to the inner member 705, the outer member 710, and/or any other suitable component of the tissue dissection assembly 702.

FIG. 8 is an enlarged isometric view of the tissue dissection assembly 702 of FIG. 7 in an expanded state in accordance with embodiments of the present technology. As illustrated in FIG. 8, a distal end section of the outer member 810 has slits or apertures that define a plurality of expandable arms 820 (identified to individually as first through third arms 820a-820c, respectively; referred to collectively as "arms 820;" also referred to as flanges or expansion members). In the illustrated embodiment, the outer member 810 includes three arms 820, but in other embodiments the outer member 810 can include one, two, or more than three arms 820. These expandable arms 820 are configured such that when the inner member 805 is pulled in a proximal direction, one or more of the expandable arms 820 expand, extend, and/or flex outwardly from a first, low-profile state to a second, expanded state to create a three-dimensional (3D) shape with a larger cross-sectional dimension (e.g., diameter) than in the first state. The 3-D shape and/or configuration of the expanded arms 820 can aid and/or facilitate dissecting tissue. The length of proximal movement of the inner member 805 can determine the size (e.g., cross-sectional dimension, width, volume of expansion) of the expanded outer member 810. An actuator in device handle assembly 11 (FIG. 1) can control the amount of pullback (proximal movement) of inner member 805, thereby controlling the size of the expanded outer member 810. For example, as discussed above with respect to FIG. 6, the inner member 805 (e.g., the tissue access component 841) can be operably coupled to the first adjustment component 675 while the outer member 810 (e.g., the tissue dissector component 842) can be operably coupled to the second adjustment component 685.

In the illustrated embodiment, the first and second arms 820a, 820b (also referred to as dissection arms 820a, 820b) extend generally outward along a first plane (also referred to as a "dissection plane") or are angled slightly inwardly (e.g., 0.1° to 15°) toward each other from the flat first plane such that the opposing, outwardly projecting arms 820a, 820b can function to dissect a vessel wall. The first and second arms 820a, 820b can contain cutting elements 825a, 825b, such as a blade or other suitable element for cutting and/or dissecting the vessel wall. The third arm 820c extends in a generally transverse manner to the plane (or planes) defined by the first and second arms 820a, 820b (e.g., 90° from to the dissection plane, between 45° and 90° from the first and second arms 820a, 820b). With this orientation, the third arm 820c (also referred to as a tensioning arm 820c) imparts tension on an interior surface of the vessel wall to facilitate dissection of the vessel wall via the cutting elements 825a, 825b on the first and second arms 820a, 820b.

As further shown in FIG. 8, the transducer 801 can be affixed to the inner member 805 (e.g., via adhesive, via a metallic weld and/or solder, embedding, and/or any other suitable attachment feature). In this configuration, actuation of the inner member 805 can also adjust the position of the transducer 801, and automatically position the transducer 801 to image the expanding arms 820 as they move radially away from the inner member 805. In some embodiments, the tissue dissection assembly 702 can include more than one transducer 801 affixed along the length of the inner member 805. Additionally, or alternatively, one or more transducers 801 can be positioned proximal or distal to the arms 820 along the outer member 810 and/or one or more transducers 801 affixed elsewhere on the tissue dissection assembly 702.

FIG. 9, for example, is an isometric view of a distal end portion 913 of a valve creation device 900 including transducers 901 (identified individually as first through third transducers 901a-c, respectively) affixed to an outer member 910 in accordance with some embodiments of the present technology. The valve creation device 900 includes several features at least generally similar to the valve creation device 700 of FIGS. 7 and 8. In the illustrated embodiment, however, the transducers 901a-c are attached individually to the corresponding first through third arms 920a-c. In some embodiments, only one or two of the arms 920 include a transducer 901, and/or one or more arms 920 can include more than one transducer 901 affixed thereon. Like the embodiments discussed above with respect to FIG. 8, the third arm 920c can be oriented between the two dissection arms 920a and 920b to create tension with a vessel wall and/or a larger dissection volume, and the height of the third arm 920c is indicative of (or partially define) the dissection pocket volume. In some embodiments, the image from third transducer 901c on third arm 920c is used to determine what size the outer member 910 should be expanded to by enabling a view of the expanded third arm 920c in relation to the vessel wall.

The affixed transducers 701, 801, 901 described with respect to FIGS. 7-9 may be one or more of multiple transducers carried by the valve creation device 10 (FIG. 1). For example, the valve creation device 10 may also include one or more additional transducers affixed to other components in the valve creation assembly 101 (e.g., positioned within and/or beneath the trough section 103 of the distal end portion 13, as shown in FIGS. 2-4).

Figure 10:
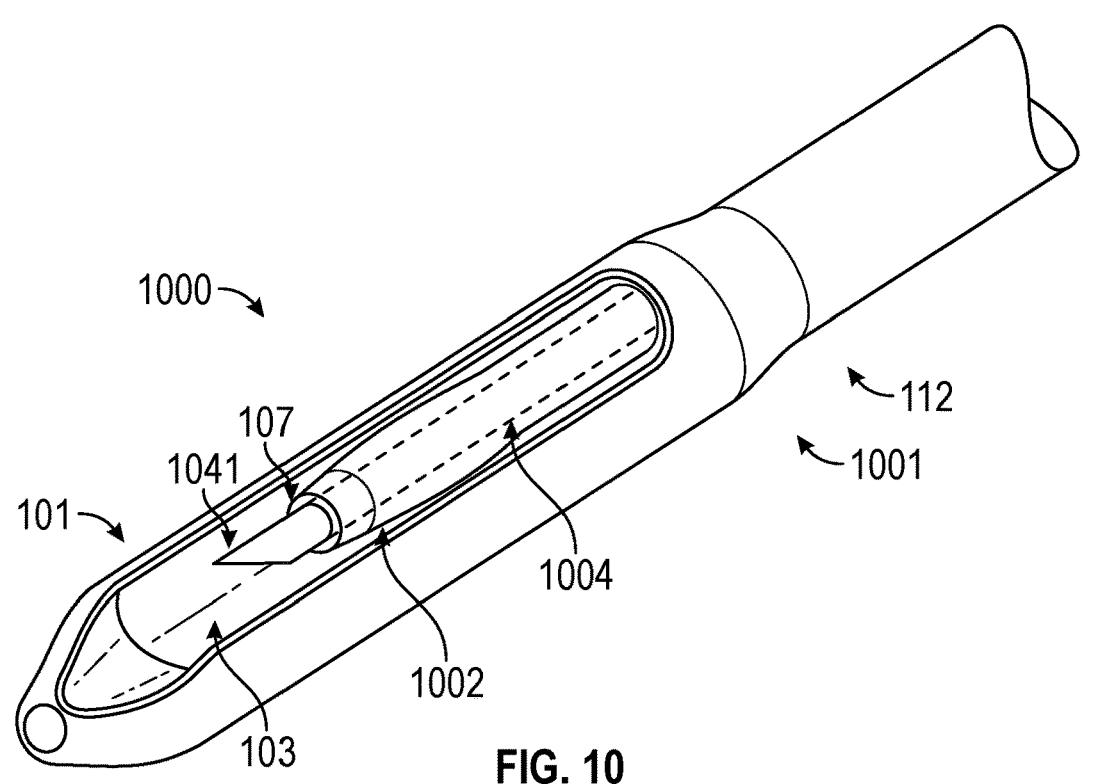
FIG. 10 is an isometric view of a distal portion of a valve creation device including an expandable balloon as a tissue dissection component in accordance with embodiments of the present technology.
Figure 11:
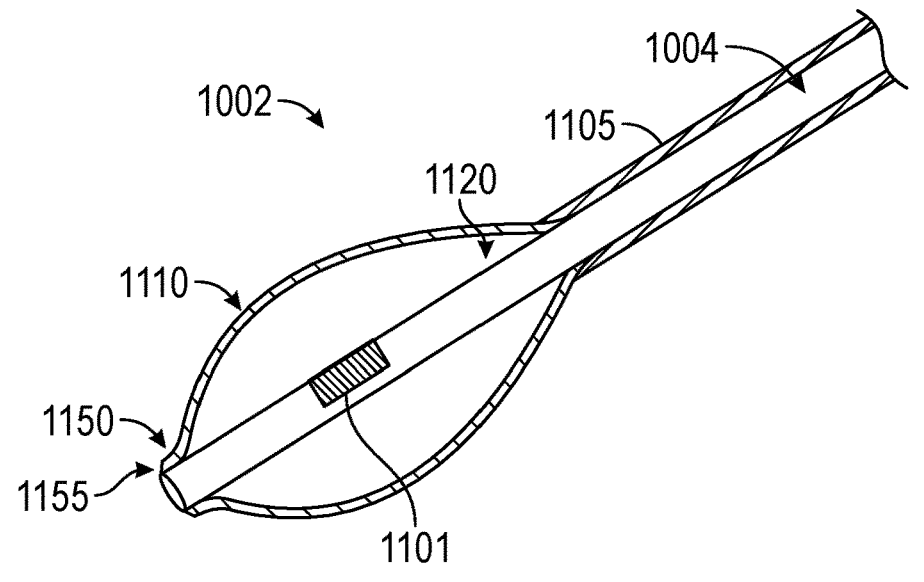
FIG. 11 is an enlarged isometric view of the expandable balloon of FIG. 10 with transducer affixed to an inner shaft in accordance with embodiments of the present technology.

FIG. 10 is an isometric view of a distal portion of a valve creation assembly 1000 having a valve creation device 1001 including an expandable balloon dissector 1002 in accordance with embodiments of the present technology, and FIG. 11 is an enlarged, partial cross-sectional view of the balloon dissector 1002 of FIG. 10. The illustrated balloon dissector 1002 can be incorporated into any of the valve creation devices described above as a tissue dissection component (e.g., in conjunction with a mechanically expandable tissue dissection assembly and/or to replace the mechanically dissection assembly and/or to replace the mechanically expandable tissue dissection assembly). As shown in FIGS.

10 and 11, the tissue access component 1041 (e.g., a needle) can be slidably disposed within a central lumen 1004 of balloon dissector 1002. Referring to FIG. 11, the balloon dissector 1002 can include an outer shaft 1105 terminating in an expandable balloon 1110 (also referred to as an "expandable member"), and an inner shaft 1120 terminating at a distal tip portion 1113. The expandable balloon 1110 can be joined together with the inner shaft 1120 at the distal tip 1150 (e.g., in a mechanical bond, heat bond, adhesive bond, or any other suitable junction) to seal the inner shaft 1120 to the expandable balloon 1110. The inner shaft 1120 includes the central lumen 1004 slidably containing the tissue access component 1041. Additionally, the distal tip 1150 can have an opening 1152 to the central lumen 1004 and a tapered leading edge 1155 that can facilitate insertion of the balloon dissector 1002 into the vessel wall between tissue layers. In some embodiments, the distal tip 1150 and/or the leading edge 1155 includes a radiopaque marker. In some embodiments, the outer shaft 1105 is omitted and the expandable balloon 1110 is affixed to the inner shaft 1120 at both its proximal and distal ends.

As further illustrated in FIG. 11, one or more transducers 1101 can be affixed to (or otherwise carried by) the inner shaft 1120 of balloon dissector 1002. For example, the inner shaft 1120 can have two lumens: a first lumen can be sized to slideably accommodate the tissue access component 1041, while a second lumen can be sized to accommodate electrical wires attached to transducer 1101. In some embodiments, the transducer 1101 is movably positioned within the inner shaft 1120. For example, the first lumen can be sized to slideably accommodate the tissue access component 1041, while the second lumen is sized to movably accommodate the transducer 1101 and a transducer shaft (e.g., the transducer shaft 310 described above with respect to FIG. 3). In various embodiments, the device 10 can additionally, or alternatively, include one or more transducers 1101 positioned on other components of the balloon dissector 1002, such as the outer shaft 1105 and/or on the surface of the expandable balloon 1110 itself.

As described above, in various embodiments, the balloon dissector 1002 may include a multi-lumen shaft (e.g., two, three, or more lumens), with a balloon affixed (e.g., bonded) to the shaft at a proximal balloon location and at a distal balloon location. In some such embodiments embodiment, one of the shaft lumens (e.g., a first lumen) has a sufficient cross-sectional area to inflate and deflate the balloon within a suitable time interval (e.g., allowing sufficient fluid flow). The first lumen (also called an inflation lumen and/or a deflation lumen) terminates at an opening that establishes fluid communication between the first lumen and the interior of the balloon. The opening can be between the two balloon-to-shaft bonds, and can be formed in the sidewall of the balloon dissector 1002 and/or extend from the first lumen to the interior of the balloon. A second lumen of the multi-lumen shaft can be large enough to accommodate the tissue access component 1041 (FIG. 10) and/or other valve formation components. In some embodiments, the balloon shaft may further include a third lumen which can be sized to accommodate electrical wires and/or a transducer shaft attached to the transducer 1101.

In any of the embodiments described above with respect to FIGS. 2-11, transducers can be integrated into the distal end portion of the valve creation device 10 by fixed attachment at select positions and/or to select components of the valve creation assembly and/or movable with respect one or more components of the valve creation assembly. Further, in some embodiments, valve creation devices configured in accordance with the present technology can include any combination of the transducers discussed above with respect to FIGS. 2-11. For example, a valve creation device can include the transducers 401 discussed above with respect to FIG. 4 (e.g., affixed beneath the trough section 103), the transducer 801 discussed above with respect to FIG. 8 (e.g., affixed to the inner member 805), and the transducers 901 discussed above with respect to FIG. 9 (e.g., (affixed to the outer member 910). The transducers on different locations of device 10 will show different images due to their different perspectives in relation to the vessel wall, the tissue dissection layers, and the various components of the valve creation device 10. In some embodiments, the signals from the different transducers can be combined via imaging processing software in the console to display one or more composite images recreated from the separate signals to provide broader views of the anatomy and/or the valve creation device 10 performing a valve creation procedure. Additionally, or alternately, one or more of the integrated transducers described above can be used in conjunction with a separate IVUS catheter situated in a lumen of valve creation device 10.

Figure 12:
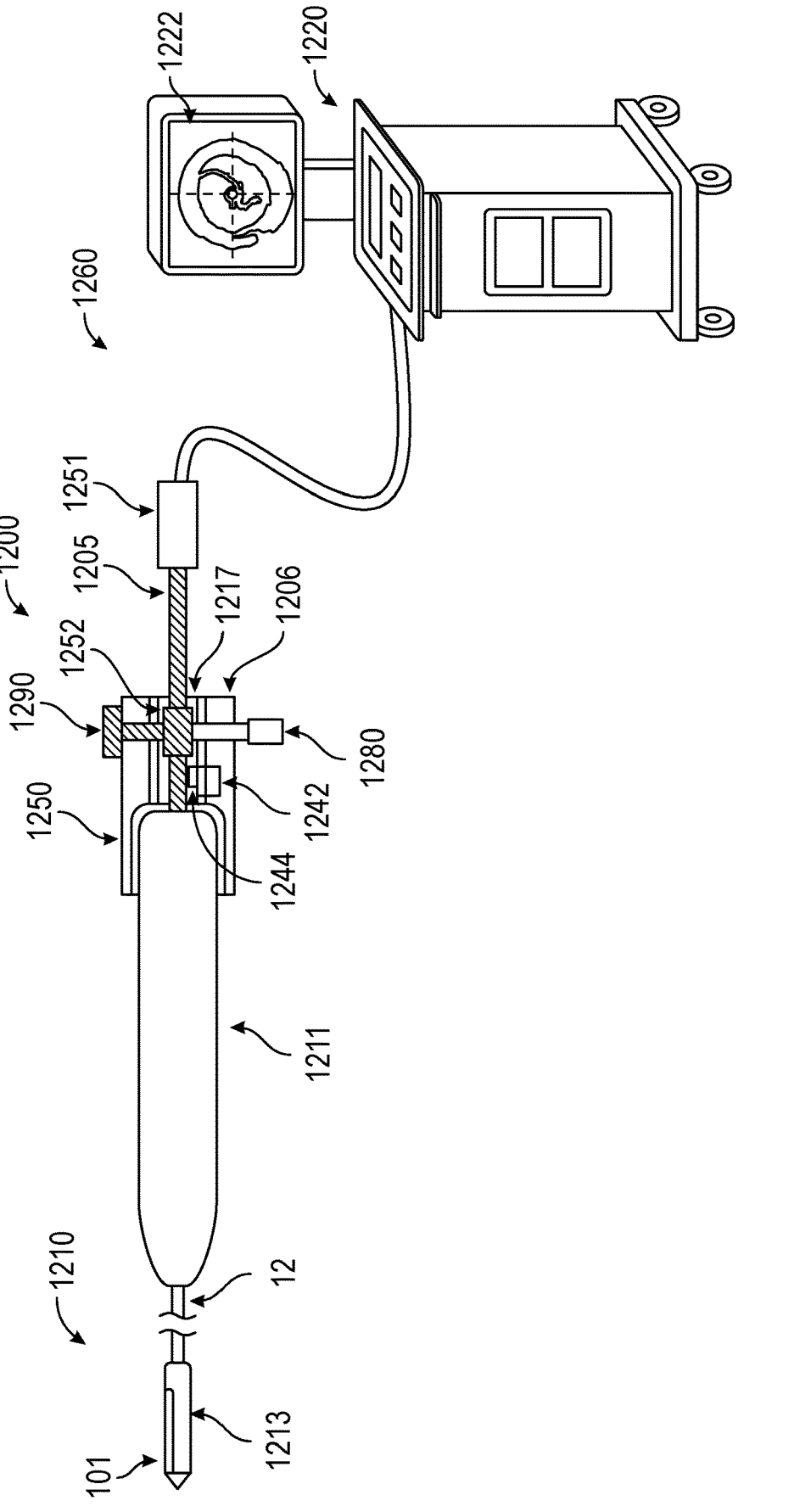
FIG. 12 illustrates a valve creation and imaging system including a valve creation device coupled to separate imaging catheter in accordance with embodiments of the present technology.

Selected Embodiments of Systems with Coupled Visualization Means and End Effectors Various embodiments of the present technology include valve creation and imaging systems that include a valve formation device, a separate IVUS system, and/or a means for coupling the valve formation device and the IVUS system together in a mechanical and/or electronic manner. The IVUS system can be the IVUS systems manufactured by Boston Scientific, Phillips, and/or other IVUS systems known to those skilled in the art. FIG. 12 illustrates a valve creation and imaging system 1200 ("system 1200") including a valve creation device 1210 coupled to an external and/or separate imaging catheter system 1260 (e.g., an IVUS catheter system) in accordance with embodiments of the present technology. In the illustrated embodiment, the imaging catheter system 1260 includes an IVUS catheter 1205 (also referred to as an "imaging catheter 1205"), an IVUS system console 1220 (also referred to as an "imaging console"), and a cable and control unit 1251. The system 1200 can further include an external coupling component 1250 used to moveably couple a handle assembly 1211 of the valve creation device 1210 to a proximal IVUS hub 1252 of the IVUS catheter 1205. The external coupling component 1250 can slideably couple the handle assembly 1211 to the IVUS catheter 1205. For example, the external coupling component 1250 can include a base 1206 and a sliding component 1217. The sliding component 1217 can move in a longitudinal direction (e.g., forward and backward) with respect to base 1206. For example, features of sliding component 1217 (e.g., rails, protrusions) can be positioned within and slide along grooves or tracks that extend along the base 1206. The handle assembly 1211 of the valve creation device 1210 is secured to base 1206, for example with a snap fit, screw mechanism, and/or a latch, and the IVUS hub 1252 is secured to sliding component 1217, for example with a snap fit, screwing mechanism, and/or a latch.

A locking mechanism 1280 on the external coupling component 50 can lock and unlock the sliding component 1217 within the base 1206, and thereby lock and unlock the position of the IVUS catheter 1205 with respect to the device handle assembly 1211. When the locking mechanism 1280 is in an unlocked state (also referred to as an unlocked position), the external coupling component 1250 allows the user to freely move the IVUS catheter 1205 relative to the handle assembly 1211; when locking mechanism 1280 is in a locked state (also referred to as a "locked position"), the position of the IVUS catheter 1205 is fixed with respect to handle assembly 1211 such that the two move in tandem. In some embodiments, movement of the IVUS catheter 1205 is accomplished by means of an actuator 1290 on external coupling component 1250. The actuator 1290 may be a slider, rotation knob, ratchet, and/or any other suitable actuation mechanism that translates the IVUS catheter 1205 with respect to device handle assembly 1211. In some embodiments, the actuator can have one or more stops that impede further movement of the IVUS catheter 1205. For example, the stops can automatically toggle the locking mechanism 1280 back into the locked state, thereby requiring the user to again unlock the locking mechanism 1280 before further actuation. The stops can be set at predefined positions for a procedure, allowing the user to quickly adjust the IVUS catheter 1205 to the predefined positions during the procedure. In some embodiments, the external coupling component 1250 may include a drive mechanism, such as a motor, which translates the IVUS catheter 1205 in a controlled manner with respect to the device handle assembly 1211. In some such motorized and/or automated embodiments, the user can select the speed and direction of translation via controls on the external coupling component 1250 and/or imaging console 1220.

Figure 13:
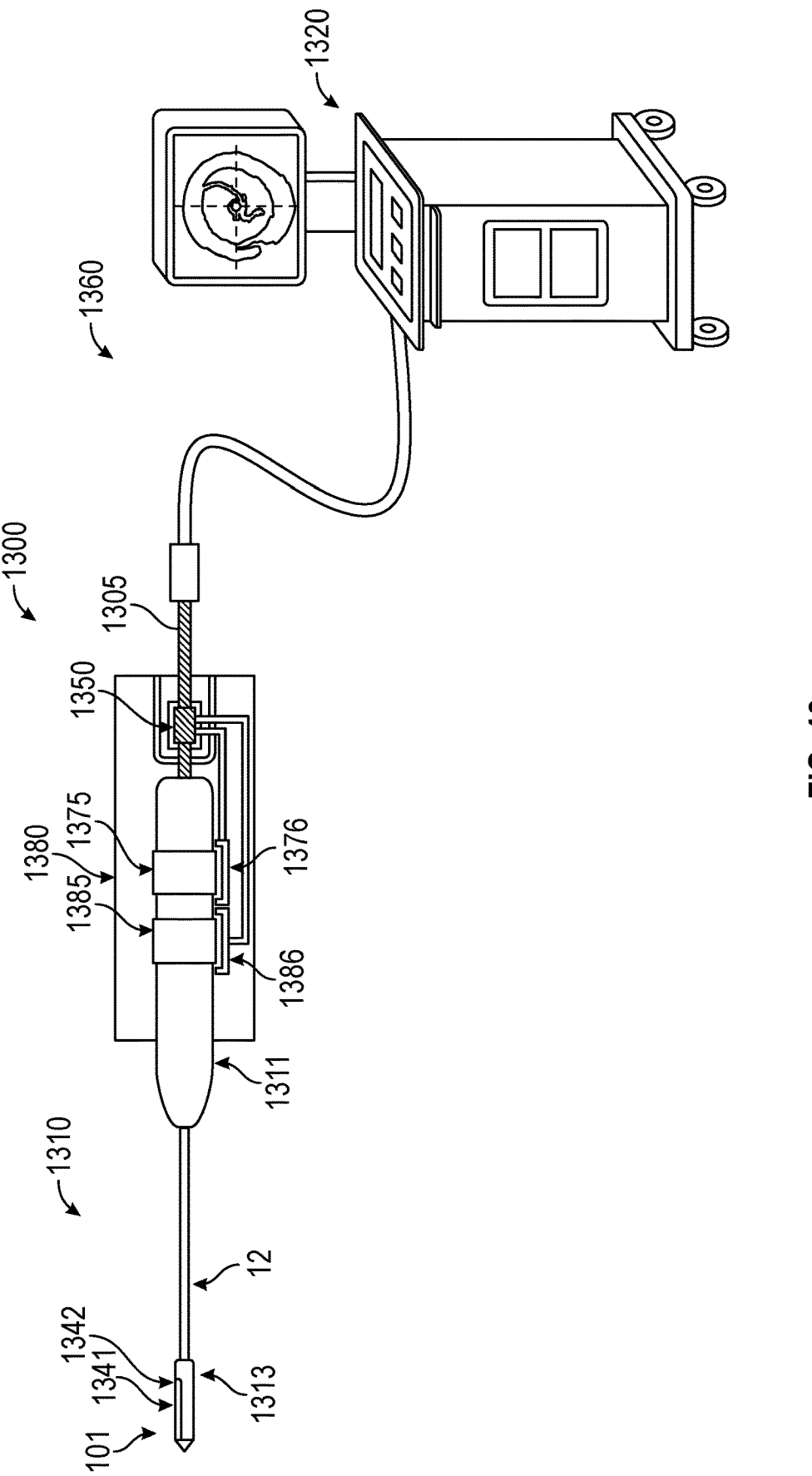
FIG. 13 illustrates a valve creation and imaging system including a valve creation device and a separate imaging catheter joined via a coupling mechanism in accordance with embodiments of the present technology.

FIG. 13 illustrates a valve creation and imaging system 1300 including a valve creation device 1310 and a separate imaging catheter system 1360 joined via an external coupling component 1380 configured in accordance with embodiments of the present technology. The external coupling component 1380 mechanically couples the IVUS catheter 1305 to a specific component of the valve creation device 1310, such as the valve creation assembly 101, the tissue access component 1341, the tissue dissector component 1342, and/or other components of the device 1310. As discussed in more detail above with respect to FIG. 6, the device handle assembly 1311 can include a first adjustment component 1375 (also referred to as a "needle knob") that advances a tissue access component 1341 and a second adjustment component 1385 (also referred to as a "dissector knob") that advances the dissector component 1342. In some embodiments, the external coupling component 1380 couples the first adjustment component 1375 to the IVUS hub 1350 with a first coupling assembly 1376. As a result, when the first adjustment component 1375 advances or retracts the tissue access component 1341, the first coupling assembly 1376 advances or retracts the IVUS catheter 1305. In some embodiments, for example, the first adjustment component 1375 can include an exterior grooved track that mates with a grooved component on the first coupling assembly 1376, which is in turn connected to the IVUS hub 1350 through one or more arms. As the first adjustment component 1375 rotates, the grooved tracks can move the needle hub 650 (FIG. 6) and the grooved component of the first coupling assembly 1376 in conjunction, thereby advancing or retracting the tissue access component 1341 and the IVUS catheter 1305 in conjunction. In various other examples, the first coupling assembly 1376 can be connected to the needle hub 650 (FIG. 6) through a groove/slot in the first adjustment component 1375; the external coupling component 1380 can mimic the motion of the needle hub 650 (e.g., through electrical signals); the external coupling component 1380 can ratchet the first adjustment component 1375 and the first coupling assembly 1376 in conjunction; and/or the motion can be linked through any other suitable means.

In some embodiments, the external coupling component 80 couples the second adjustment component 1385 to the IVUS hub 1350 with a second coupling assembly 1386. In some embodiments, the second coupling assembly 1386 can function similar to the first coupling assembly 1376 to link the motion of the dissector hub 680 (FIG. 6) with the motion of the IVUS hub 1350. As a result, when then the second adjustment component 1385 advances or retracts, the tissue dissector component 1342, the second coupling assembly 1386 advances or retracts the IVUS catheter 1305.

In some embodiments, the external coupling component 1380 allows selective coupling of the IVUS catheter 1305 to either the tissue access component 1341 or the dissector component 1342 at different stages of the procedure. In some embodiments, the external coupling component 1380 can additionally decouple the IVUS catheter 1305 from either of the first and second coupling assemblies 1376, 1386, thereby allowing independent movement of IVUS catheter 1305 during selective stages of the procedure.

Selected Embodiments of Systems with Position Sensing

Various aspects of the present technology are directed to valve creation and imaging systems that include means for detecting and relaying position information or data from one or more transducers (e.g., any of the transducers described above with respect to FIGS. 2-11) and/or other imaging components with respect to a tissue manipulation device (e.g., a valve creation device). In various embodiments, one or more transducers are on a separate IVUS catheter (e.g., the IVUS catheter 605 described above with respect to FIGS. 12 and 13), and/or one or more IVUS transducers are integrated into the valve creation device 10 (e.g., as described above with respect to FIGS. 2-11).

In some embodiments, the valve creation and imaging systems with position information include position sensors integrated into an external coupling component that positionally couples the valve creation device to the IVUS catheter. For example, the system 1200 of FIG. 12 illustrates a system with position sensor 1242 and position sensor 1244 (referred to collectively as "sensor couple 1242, 1244"). As shown in FIG. 12, the sensor couple 1242, 1244 are integrated into the external coupling component 1250 such that the sensor couple 1242, 1244 can determine the position of the IVUS catheter transducer (at the distal end portion of the IVUS catheter 605) with respect to the valve creation device 10. In the illustrated embodiment, the position sensor 1242 is on the base 1206 of the external coupling component 1250 (e.g., embedded in, affixed to a surface of, and/or otherwise attached to the base 1206). The position sensor 1244 on the sliding component 1217 of the external coupling component 1250 (e.g., embedded in, affixed to a surface of, and/or otherwise attached to the sliding component 1217). The position sensor 1242 is operably coupled with the position sensor 1244 to output position data based on the position of the position sensor 1244 with respect to the position sensor 1242. The sensor couple 1242, 1244 can comprise two or more sensors that are configured (e.g., sized, shaped, arranged, programmed) to sense and/or detect the position of one sensor or sensor component with respect to one or more other sensors and/or sensor components using optical, magnetic, and/or electrical technology. The sensor couple 1242, 1244 can include any one of these types of position sensing mechanisms or a combination of two or more sensing mechanisms. For example, the position sensor 1242 may generate a magnetic field which senses position of a magnetic component in the position sensor 1244. In other embodiments, the position sensor 1242 is an optical detector which detects an encoded optical pattern positioned on sliding component 1217. The optical pattern can be configured to provide position information to the optical detector The output of the position sensor 1242 can be communicated to the imaging console 1220 (e.g., via a wired or wireless connection), enabling the imaging console 1220 to determine and/or display position of the IVUS catheter along with (or instead of) the IVUS image on the screen 1222. In some embodiments, the catheter position is additionally, or alternatively, displayed on the external coupling component 1250 itself.

In various embodiments, the valve formation and imaging systems disclosed herein can also detect, monitor, and/or display the position of components of the valve creation assembly. For example, the valve formation and imaging systems can detect and display the position of the tissue access component and/or the tissue dissection component. Examples of systems for detecting, monitoring, and/or displaying the position of components of the valve creation assembly are illustrated with respect to FIGS. 14 and 15.

Figure 14:
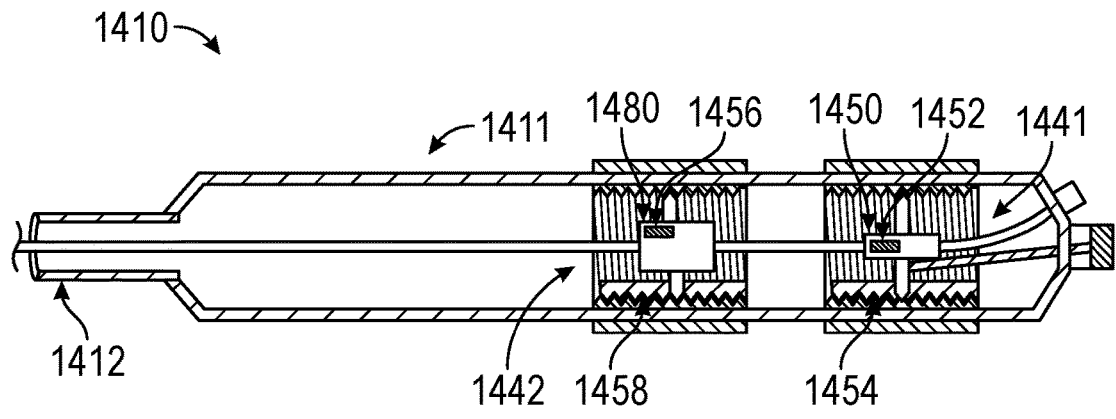
FIG. 14 is a partial cross-sectional view of a valve creation device handle assembly including position sensors configured in accordance with embodiments of the present technology.

FIG. 14 is a partial cross-sectional view of a handle assembly 1411 that includes one or more sensors for detecting positional information of device components in accordance with embodiments of the present technology. As shown in FIG. 14, a first position sensor 1452 can be located at or positioned on the needle hub 1450 of tissue access component 1441 with a corresponding sensor coupler 1454 located in a fixed position within the body of the device handle assembly 1411 (also referred to collectively as "tissue access sensor couple 1452, 1454"). Similarly, a second position sensor 1456 can be located at or positioned on the dissector hub 1480 of the tissue dissection component 1442 with a corresponding sensor coupler 1458 located in a fixed position within the body of the device handle assembly 1411 (also referred to collectively as "dissector sensor couple 1456, 1458"). The first and second position sensors 1452, 1454 can move (e.g., translate proximally and distally along the longitudinal axis of the device 1410) together with their respective hubs 1450, 1480, while the corresponding sensor couplers 1456, 1458 remain fixedly positioned inside or on the handle assembly 1411. The tissue access sensor couple 1452, 1454 can determine and/or communicate positional information (absolute or relative) of the tissue access component 1441, while the dissector sensor couple 1456, 1458 can determine and/or communicate positional information (absolute or relative) of the tissue dissection component 1442. In various embodiments, the handle assembly 1411 can include additional sensor couples that detect positional data of other components of the valve formation device 1410.

In an exemplary procedure, position information from the sensor couple 1242, 1244, the tissue access sensor couple 1452, 1454, and/or dissector sensor couple 1456, 1458, can all be transmitted to the imaging console 20, 620 (FIGS. 1, 12 and 13). There, the positional data can be processed and presented to the user in a format that provides relevant positional information before, during, and/or after a valve formation procedure. For example, the imaging console 20, 620 (FIGS. 1, 12 and 13) can display a graphic that illustrates the position of any transducer (FIGS. 2-9 and 11) with respect to the distal tip (e.g., a needle tip) of the tissue access component 41 during advancement of tissue access component 41 into the vessel wall, and then illustrate the position of the transducer with respect to dissector tip during advancement and/or actuation of tissue dissection component 42. These graphical user interfaces can depict images of the actual device components and the transducer, as well as their relative position within the vessel. In some embodiments, the graphical user interface can graphically illustrate (e.g., via different indicators or colors) locations of the components within the vessel and/or with respect to each other. In some embodiments, the imaging console 20, 1220, 1320 (FIGS. 1, 12 and 13) tracks this movement and/or position data throughout the procedure and/or displays record of the movement and/or position data throughout the procedure to the user.

In some embodiments, the valve creation and imaging systems disclosed herein additionally, or alternatively, include position sensors integrated with the valve creation device 10 (e.g., along the distal end portion 13 of the catheter shaft 12 and/or integrated into the valve creation assembly 110). In such embodiments, the position sensors can directly sense positional data of various components of the valve creation device 10.

Figure 15:
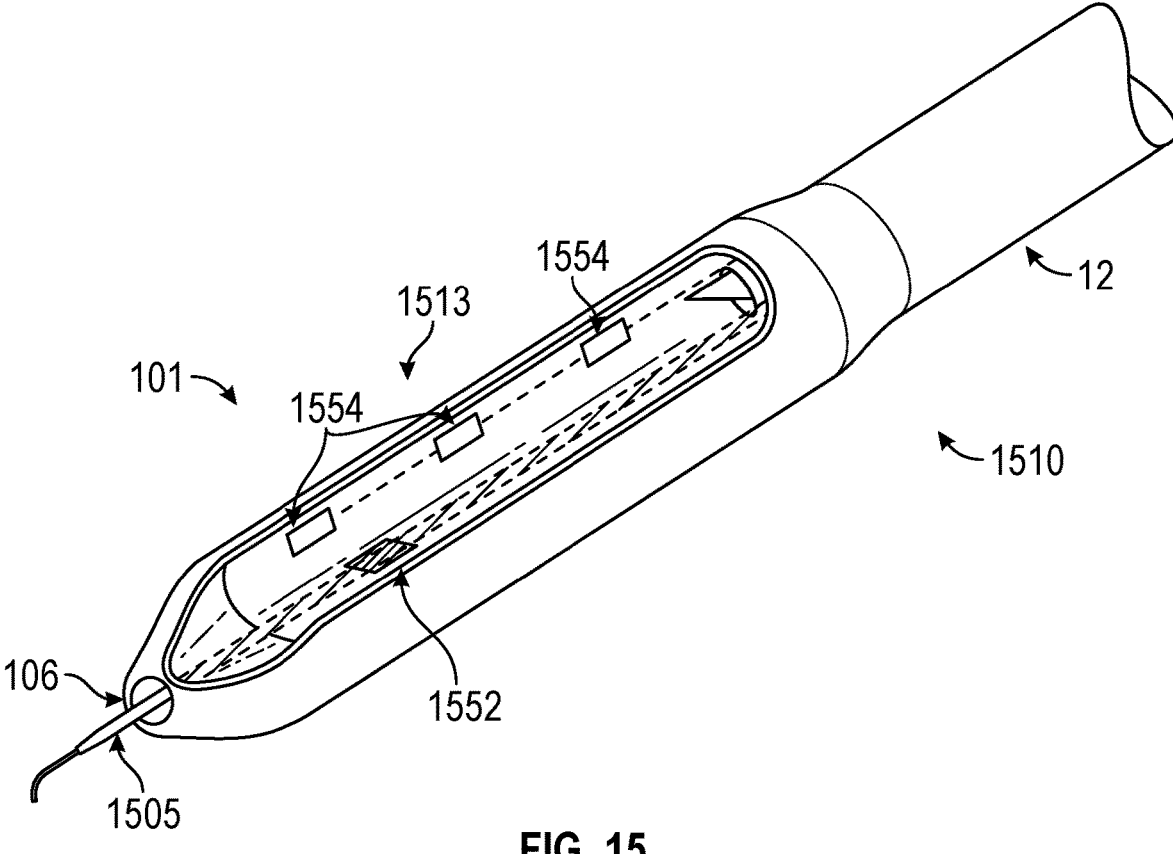
FIG. 15 is an isometric view of a distal end portion of a valve creation device including position sensors configured in accordance with embodiments of the present technology.

FIG. 15 is an isometric view of the distal end portion 1513 of the valve creation device 1510 configured in accordance with embodiments of the present technology. In the illustrated embodiment, the valve creation device 1510 includes position sensors integrated into the valve creation assembly 101. The position sensors can include one or more transmitters 1552 on the IVUS catheter 1505 and one or more receivers 1554 located at the distal end portion 1513 of the valve creation device 1510. The transmitters 1552 are configured to transmit signals related to their position, while the receivers 1554 are configured to receive the signals from the transmitters 1552. In some embodiments, the transmitter(s) 1552 are integrated into and/or coupled with the transducer chip to streamline the profile (i.e., reduce or minimize) of the IVUS catheter 1505. In some embodiments, each transmitter 1552 is a magnet, and the receivers 1554 create a magnetic field to sense movement of the magnet(s) 1552 (i.e., the transmitters) within the field. The data from the transmitters 1552 and the receivers 1554 can be received by the imaging console 20, 1220, 1320 (FIGS. 1, 12 and 13) via a wired and/or wireless connection. The imaging console 20, 1220, 1320 (FIGS. 1, 12 and 13) can the process the data to determine the position of the IVUS catheter 1505 (and therefore the IVUS transducers) with respect to the valve creation assembly 110 at the distal end portion 1513 of the valve creation device 1510.

In some embodiments, the valve creation device 1510 disclosed herein includes one or more mechanisms to mechanically advance or retract individual components, such as the tissue access component 41 and/or the tissue dissection component 42 (FIG. 1). Mechanical movement of the tissue access component 41 (FIG. 1), the tissue dissection component 42 (FIG. 1), and/or the IVUS catheter 1505 within the catheter shaft 12 (FIG. 1) can be done manually and/or automatically, as well as via local actuation and/or remote actuation. Further, the mechanism(s) for imparting mechanical translation of the various system components can be integrated with the linear translation of the imaging transducer.

Figure 16:
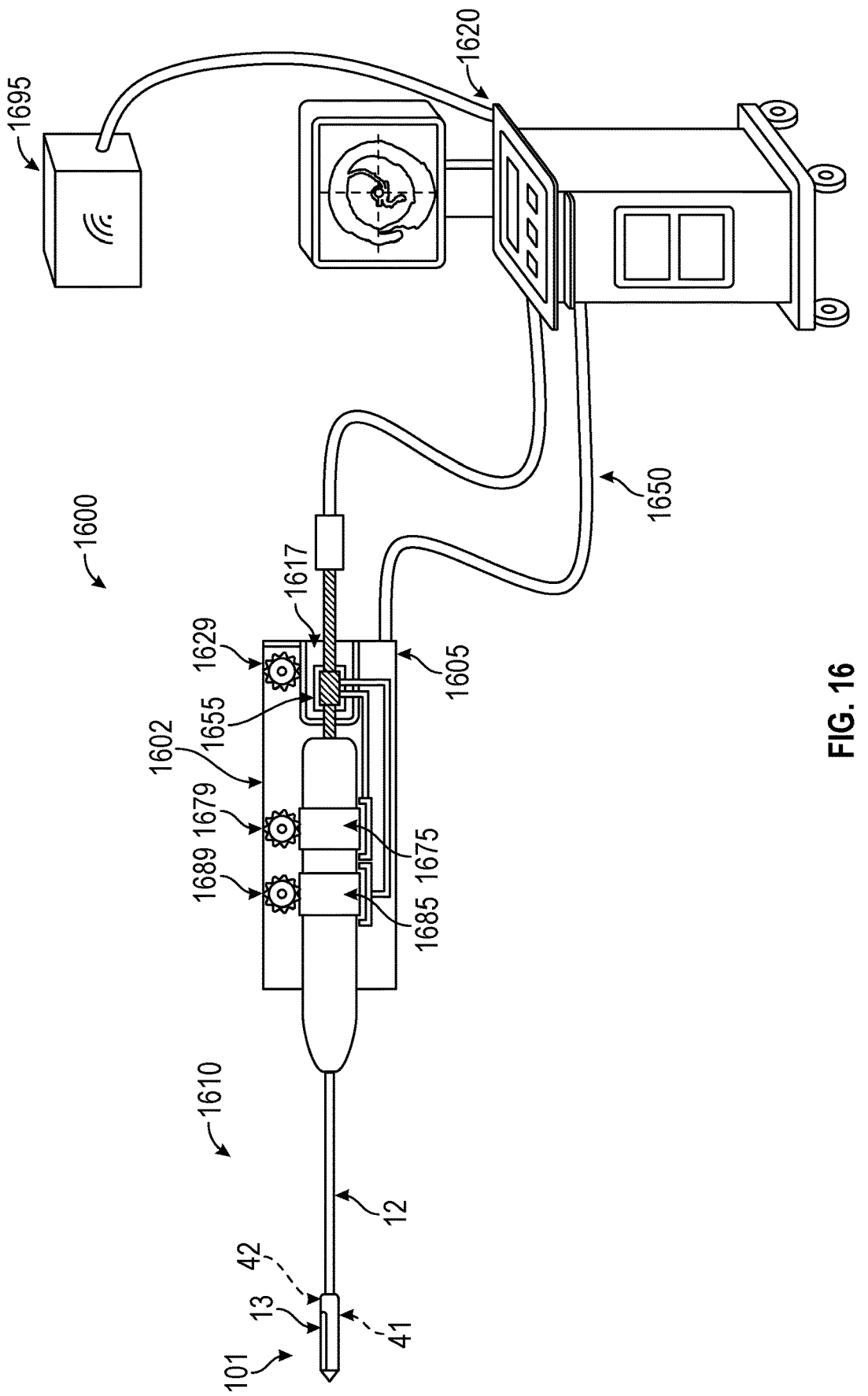
FIG. 16 illustrates a valve creation and imaging system including automatic positioning of valve creation components and an imaging catheter in accordance with embodiments of the present technology.

FIG. 16 illustrates a valve creation and imaging system 1600 including a mechanism for mechanically translating the various system components in accordance with some embodiments of the present technology. In the illustrated embodiment, the valve creation and imaging system 1600 includes a control assembly 1602 (also referred to as a "control unit 1602") operably connected to the valve creation device 1610. The control unit 1602 includes a first drive mechanism 1679 operably coupled to a first adjustment component 1675 to drive linear movement (e.g., advances or retracts) of a tissue access component 41 (FIG. 6). For example, rotation of the first drive mechanism 1679 can cause the first adjustment component 1675 to rotate axially, thereby driving the tissue access component 41 (FIG. 6) along a linear path. The control unit 1602 also includes a second drive mechanism 1689 coupled to the second adjustment component 1685 to drive linear movement of the tissue dissection component 42. For example, rotation of the second drive mechanism 1689 can cause the second adjustment component 1685 to rotate axially, thereby driving the tissue access component 41 (FIG. 6) along the linear path. As further illustrated in FIG. 16, the control unit 1620 can further include a base component 1605 and a sliding component 1617 that moves forward and backward along the linear path with respect to the base component 1605, and an IVUS hub 1655 (also referred to as an "imaging hub 1655") can be secured (releasably or fixedly) to the sliding component 1617. The control unit 1620 can further include a third drive mechanism 1629 operably coupled to the sliding component 710 to drive movement of the IVUS hub 1655 (and the imaging component attached thereto) with respect to valve creation device 1610. The IVUS hub 1655 can be operably coupled to a component of a separate IVUS catheter (e.g., as discussed above with respect to FIGS. 12-15) and/or of an IVUS transducer assembly integral to the valve creation device 1610 (e.g., as discussed above with respect to FIG. 211).

In some embodiments, the first through third drive mechanisms 1679, 1689, and 1629 include gears operably coupled to one or more corresponding motors (e.g., servomotors) within the control assembly 1602. The gears can engage with features of the component with which they interface (e.g., the adjustment components 1675 or 1685 or the sliding component 1617) to move the respective component in the desired direction (proximally or distally) along the linear path. In other embodiments, the drive mechanisms 1679, 1689, and 1629 can include other suitable automated driving mechanisms.

During an operation, a user can select to move (e.g., advance or retract) the tissue access component 41, the tissue dissection component 42, and/or the imaging component (e.g., a separate imaging catheter or a movable transducer component) using controls of the control assembly 1602 (e.g., knobs, buttons, sliders, wheels, switches, touch screen controls, keyboard controls, or any other suitable controls). In some embodiments, the control assembly 1602 is connected to the imaging console 1620 via a cable 1650 and/or other connection mechanism (e.g., a wireless connection). The imaging console 1620 can receive user inputs to selectively control the automated movement of the system components (either in tandem or individually). The user interface (e.g., a touch screen, a keyboard and monitor) of the imaging console 1620 can be large and thus well suited for setting parameters of the control assembly 1602.

In some embodiments, the control assembly 1602 with monitored and/or controlled by a user in the procedure or operating room with direct contact to the valve creation device 1610 and the patient. In various embodiments, the control assembly 1602 can be monitored and/or controlled by a remote user outside of the procedure room. For example, the control assembly 1602 can be communicatively connected to a computer 1695 with a connection to the internet, phone line, local area network (LAN), shortrange radio frequency (e.g., Bluetooth), or other suitable external communication means. In some embodiments, the control assembly 1602 can be controlled by either an in-person user or a remote user. The remote user can also have access to additional information about the patient and/or procedure, such as IVUS and fluoroscopic images, position information associated with some or all device components, a view of the room in general and the valve creation device 1610 specifically, and/or patient monitoring information. The ability to remotely control the system 1600 can be useful for training and/or proctoring purposes, or to reduce the number of in-room users required to perform a procedure. In some methods of use, the remote user simply monitors the position of IVUS catheter, the tissue access component 41, and the tissue dissection component 42, and communicates advice to the clinician in the procedure room as needed. In additional methods of use, the remote user can manually or automatically advance the system components, using a secondary control unit at the remote user's location. In some embodiments, portions of the movement of the various system components can be automated via algorithms stored at the control assembly 1602 and/or at a remote database and control interface.

In some embodiments with mechanical control of component positions, the position sensors discussed above with respect to FIGS. 13-15 are omitted as control of both the transducer advancement and tissue access component advancement will ensure that the two components maintain a fixed position with respect to each other. In some embodiments, the position sensors can still provide information that facilitates the procedure. For example, if the user wishes to have the option to manually advance the tissue access component 41 in addition to having it advance automatically.

In some embodiments, the valve creation and imaging systems disclosed herein can include passive position sensing means. For example, one or more components of the valve creation devices disclosed herein can include a passive feature that is distinctive to the IVUS transducer, such as an area that is particularly echogenic and shows up as a bright spot on the ultrasound image. The valve creation devices can also, or alternatively, include one or more markers made of materials visible via ultrasound (e.g., gold or other metals) and/or markers defined by a roughened surface. In some embodiments, a pattern of markings may be used to indicate the position of a component, for example groups of markings can be spaced apart from each other at predefined intervals (e.g., 1 cm apart), wherein one marking (e.g., ".") indicates the distal end of a component, a group of two markings (e.g., ". .") indicates 1 cm proximal to the distal end, a group of three markings (e.g., " . . . ") indicates 2 cm from the distal end, and so on. In some embodiments, groups of markers are spaced apart from each other at other distance intervals (e.g., 3 mm apart, or some similar useful distance). The markers can be located on one or more of: the distal end portion of the valve creation device, the tissue access component, and/or the dissector component. The markers can also be spaced radially apart from each other rather than longitudinally to represent relative rotational positioning, if the component has sufficient radius to make distinct marker patterns radially, for example the distal end portion of device.

Selected Embodiments of End Effectors with Integrated or Coupled Angioscopy Devices Valve formation and imaging systems disclosed herein can also include systems having a valve formation device with a channel for delivering of an angioscopic catheter to the distal end portion of the device and/or beyond the distal terminus. The angioscopic catheter can be used to visualize the interior of the vessel wall before, during, and after the valve formation procedure to provide guidance and assessment of the procedure. The valve formation device can further include a flush lumen to flush saline through the blood vessel to enhance visualization.

In some embodiments, the valve creation device 10 includes an expandable member (e.g., a compliant balloon) on one side of the catheter shaft 12 such that the expandable member can be expanded (e.g., inflated) to press the opposite side of the distal end portion 13 in apposition with the interior vessel wall. For example, the valve creation device 10 can use a balloon as a means to gain vessel wall apposition during the tissue access step of a valve formation procedure. In these embodiments, the same balloon can be retracted and inflated proximal to the site of valve formation site, thereby facilitating flushing and blood-clearing of the site for angioscopic visualization of the valve formation steps.

In some embodiments, the valve formation device 10 has integrated angioscopic capabilities. For example, optical fibers may be contained in the catheter shaft 12 and terminate at a point on the distal end portion 13 of the valve formation device 10. In these and other embodiments, the optical fibers are contained within a sleeve to create an optical component that is slideably received within the catheter shaft 12 of the valve creation device 10 such that the tip of the optical component may be positioned proximally or distally (forwards or backwards) as the imaging requirement of the procedure dictates.

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A tissue manipulation and imaging device, comprising:
a handle assembly;
a catheter shaft having a proximal end portion coupled to the handle assembly and a distal end portion;
an end effector assembly at the distal end portion of the catheter shaft, wherein the end effector assembly is configured to manipulate tissue within a vessel wall;
an imaging transducer at the distal end portion of the catheter shaft; and
one or more position sensors coupled to the handle assembly and configured to determine positions of a distal end portion of the tissue manipulation device relative to the imaging transducer.

2. The tissue manipulation and imaging device of example 1 wherein the end effector assembly is a valve formation assembly configured to access the vessel wall and dissect a portion of the vessel wall to form an autologous valve leaflet.

3. The tissue manipulation and imaging device of any of examples 1 and 2 wherein:
the end effector assembly comprises a trough section; and
the imaging transducer is embedded in the trough section.

4. The tissue manipulation and imaging device of any of examples 1-3 wherein the imaging transducer comprises a moveable transducer shaft and a transducer positioned at a distal end of the transducer shaft, and wherein the transducer shaft is configured to translate the transducer along a length of the distal end portion.

5. The tissue manipulation and imaging device of example 4, further comprising a position sensor coupled to the transducer shaft and positioned in the handle assembly, wherein the position sensor is configured to detect location data of the transducer relative to the end effector assembly.

6. The tissue manipulation and imaging device of any of examples 1-5 wherein:

the end effector assembly comprises a trough section having a plurality of windows;

the imaging transducer comprises a plurality of transducer chips embedded in the corresponding plurality of windows and configured to be selectively activated depending upon stages in the valve formation procedure and positions of components of the valve formation assembly.

7. The tissue manipulation and imaging device of any of examples 1-6 wherein:

the end effector assembly comprises a tissue access component and a tissue dissection component configured to slide over the tissue access component;

the imaging transducer is movable along a length of the distal end portion of the catheter shaft; and the imaging transducer is positionally coupled to the to the tissue access component at the handle assembly.

8. The tissue manipulation and imaging device of any of examples 1-7 wherein:

the end effector assembly comprises a tissue access component and a tissue dissection component configured to slide over the tissue access component;

the imaging transducer is movable along a length of the distal end portion of the catheter shaft; and the imaging transducer is positionally coupled to the to the tissue access component in a first state and positionally coupled to the to the tissue dissection component in a second state, the imaging transducer moves together with the tissue access component in the first state and moves together with the tissue dissection component in the second state.

9. The tissue manipulation and imaging device of any of examples 1-8 wherein:

the end effector assembly comprises a tissue access component and a tissue dissection component configured to slide over the tissue access component, the tissue dissection component having an outer member, an inner member slideably received and coupled to the outer member, and a plurality of expandable arms on the outer member, wherein the plurality of expandable arms are configured to project radially outwardly from the inner member when the inner member moves proximally relative to the outer member;

the imaging transducer is integrated into the tissue dissection component; and the imaging transducer is on the inner member.

10. The tissue manipulation and imaging device of claim any of examples 1-9 wherein:

the end effector assembly comprises a tissue access component and a tissue dissection component configured to slide over the tissue access component, the tissue dissection component having an outer member, an inner member slideably received and coupled to the outer member, and a plurality of expandable arms on the outer member, wherein the plurality of expandable arms are configured to project radially outwardly from the inner member when the inner member moves proximally relative to the outer member;

the imaging transducer is integrated into the tissue dissection component; and the imaging transducer comprises a plurality of transducers coupled to the corresponding plurality of expandable arms.

11. The tissue manipulation and imaging device of claim any of examples 1-10 wherein:

the end effector assembly comprises a tissue access component and a tissue dissection component configured to slide over the tissue access component, the tissue dissection component comprising a shaft and an expandable balloon at a distal end of the shaft; and the imaging transducer is integrated into the shaft.

12. A tissue manipulation and imaging system comprising:

a tissue manipulation device comprising a handle assembly, a catheter shaft having a proximal end portion coupled to the handle assembly and a distal end portion, a lumen extending through the catheter shaft, and an end effector assembly at the distal end portion of the catheter shaft, wherein the end effector assembly is configured to manipulate tissue in a vessel wall, and wherein the lumen is configured to slidably receive an IVUS catheter; and an external coupling component comprising— a base fixedly coupled to the handle assembly, a sliding component coupled to the base and configured to be operably coupled to a portion of the IVUS catheter, and a locking mechanism operably coupled to the sliding component and the base, wherein— when the locking mechanism is in an unlocked state, the sliding component is free to move proximally and distally relative to a portion of the handle assembly, and when the locking mechanism is in a locked state, the sliding component is fixed relative to the portion of the handle assembly.

13. The tissue manipulation and imaging system of example 12 wherein:

the tissue manipulation device comprises a tissue access component and a tissue dissection component configured to slide over the tissue access component;

the handle assembly comprises a tissue access knob to control movement of the tissue access component and a dissector knob to control movement of the tissue dissector component; and the external coupling component comprises a first coupling member coupling movement of the IVUS hub to the tissue access knob and a second coupling member coupling movement of the IVUS hub to the dissector knob.

14. The tissue manipulation and imaging system of any of examples 12 and 13 further comprising at least one position sensor carried by the external coupling component, wherein the at least one position sensor is configured to detect positions of a distal end portion of the IVUS catheter relative to the distal end portion of the tissue manipulation device.

15. The tissue manipulation and imaging system of any of examples 12-14 further comprising at least one position sensor carried by the handle assembly, wherein the at least one position sensor is configured to detect positions of a distal end portion of the IVUS catheter relative to the distal end portion of the tissue manipulation device.

16. The tissue manipulation and imaging system of any of examples 12-15 wherein the end effector assembly comprises a trough section, and wherein the tissue manipulation and imaging system further comprises:

multiple receivers positioned along a longitudinal section of the trough section, wherein the multiple receivers are configured to detect transmitters at a distal end portion of the IVUS catheter to identify locations of the IVUS catheter as the IVUS catheter moves along the trough section.

17. The tissue manipulation and imaging system of any of examples 12-16, further comprising a control assembly having a motor for mechanically translating components of the tissue manipulation device and the IVUS catheter.

18. A method for forming an autologous valve leaflet in a vessel wall, the method comprising:

intravascularly advancing a distal end portion of a vessel access device to a target site within a vessel, wherein the distal end portion comprises a trough section and an exit port positioned proximal to and aligned with the trough section;

deploying a needle distally through the exit port such that the needle is positioned along the trough section and moves in a direction aligned with a longitudinal axis of the trough section;

detecting a first position of the needle relative to an imaging transducer at the distal end portion of the vessel access device;

advancing the needle at least partially into the vessel wall at a location axially aligned with the imaging transducer;

determining a second position of the needle relative to the imaging transducer, the second position corresponding to the needle after at least partially penetrating the vessel wall; and obtaining images from the imaging transducer while advancing the needle to visualize the vessel wall during needle penetration.

19. The method of example 18, further comprising:

moving the imaging transducer within a transducer lumen of a catheter shaft of the vessel access device such that the imaging transducer moves relative to the longitudinal axis of the trough section; and aligning the imaging transducer with a distal tip of the needle during imaging.

20. The method of any of examples 18 and 19, further comprising further comprising detecting a position of the imaging transducer relative to a distal terminus of the vessel access device.

21. The method of any of examples 18-20 wherein the imaging transducer is one of multiple imaging transducers affixed along the trough section of the vessel access device, and wherein the method further comprises activating one of the multiple imaging transducers based on a position of the needle relative to the multiple imaging transducers.

22. The method of any of examples 18-21, further comprising coupling the imaging transducer to the needle such that the imaging transducer and the needle move in tandem.

23. The method of example 22, further comprising decoupling the imaging transducer from the needle such that the imaging transducer and the needle move relative to each other.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. The various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A method for forming an autologous valve leaflet in a vessel wall, the method comprising:

intravascularly advancing a distal end portion of a vessel access device to a target site within a vessel, wherein the distal end portion comprises a trough section and an exit port positioned proximal to and aligned with the trough section;

deploying a needle distally through the exit port such that the needle moves in a direction aligned with a longitudinal axis of the trough section;

positionally coupling an imaging transducer to the needle such that the imaging transducer and the needle move in tandem;

while the imaging transducer is coupled to the needle, advancing the needle distally with respect to the exit port of the vessel access device and at least partially into the vessel wall at a location aligned with the trough section of the vessel access device along an axis orthogonal to the longitudinal axis, wherein the needle advances independently from the vessel access device;

determining a position of the needle relative to the imaging transducer while advancing the needle after at least partially into the vessel wall;

obtaining images from the imaging transducer while advancing the needle to visualize the vessel wall during needle penetration;

positionally coupling the imaging transducer to a second component such that the imaging transducer and the second component move in tandem;

while the imaging transducer is coupled to the second component, advancing the second component distally with respect to the exit port of the vessel access device and at least partially into the vessel wall at a location aligned with the trough section of the vessel access device along an axis orthogonal to the longitudinal axis, wherein the second component advances independently from the vessel access device and the needle; and obtaining images from the imaging transducer while advancing the second component to visualize the vessel wall during dissection.

2. The method of claim 1, wherein:

the imaging transducer is movable within a transducer lumen of a catheter shaft of the vessel access device such that the imaging transducer moves relative to the longitudinal axis of the trough section; and coupling the imaging transducer to the needle comprises aligning the imaging transducer with a distal tip of the needle.

3. The method of claim 1, further comprising detecting a position of the imaging transducer relative to a distal terminus of the vessel access device.

4. The method of claim 1 wherein the imaging transducer is a first imaging transducer, wherein the distal end portion further comprises multiple second imaging transducers affixed along the trough section of the vessel access device, and wherein the method further comprises activating one of the multiple second imaging transducers based on a position of the needle relative to the multiple second imaging transducers.

5. The method of claim 1, further comprising decoupling the imaging transducer from the needle such that the imaging transducer and the needle move relative to each other.

6. The method of claim 1, further comprising:

advancing a tissue dissection component distally to access a space in the vessel wall through an opening created by the needle; and obtaining images from the imaging transducer while dissecting the vessel wall with the tissue dissection component to visualize the vessel wall during dissection.

7. The method of claim 6, further comprising:

before advancing the tissue dissection component distally to access the space in the vessel wall, positionally coupling the imaging transducer to the tissue dissection component.

8. The method of claim 1, further comprising determining a position of a distal end of the needle relative to the distal end portion of the vessel access device after at least partially penetrating the vessel wall.

9. The method of claim 1, further comprising determining a position of the imaging transducer relative to a distalmost end of the trough section while advancing the needle at least partially into the vessel wall.

10. A method for imaging intravascular operations of a catheter device, the method comprising:

intravascularly advancing a distal end portion of a catheter shaft adjacent to a target location in a vessel, wherein the distal end portion comprises a trough section and an exit port positioned to direct tools into the trough section;

positionally coupling an imaging transducer to a first component;

advancing the first component through the exit port and into the trough section while the imaging transducer is positionally coupled to the first component;

obtaining images from the imaging transducer while advancing the first component to visualize operations of the first component;

positionally coupling the imaging transducer to a second component such that the imaging transducer and the second component move in tandem;

advancing the second component through the exit port and into the trough section while the imaging transducer is positionally coupled to the second component; and obtaining images from the imaging transducer while advancing the second component to visualize the operations of the second component.

11. The method of claim 10 wherein the imaging transducer is movable along a longitudinal axis of the distal end portion and configurable between at least a first state and a second state, wherein:

in the first state, the imaging transducer is positionally coupled to the first component;

in the second state, the imaging transducer can move along the longitudinal axis independently from the first component; and positionally coupling the imaging transducer to the first component comprises transitioning the imaging transducer from the second state to the first state.

12. The method of claim 10 wherein the first component is configured to puncture a vessel wall at the target location, and wherein the second component is configured to access the vessel wall over the first component.

13. The method of claim 12 wherein:

the imaging transducer is a first imaging transducer, wherein the second component includes one or more second imaging transducers; and the method further comprises obtaining images from the one or more second imaging transducers while accessing the vessel wall to visualize a space in the vessel wall.

14. The method of claim 12 wherein:

the imaging transducer is a first imaging transducer;

the first component includes one or more second imaging transducers; and the method further comprises obtaining images from the one or more second imaging transducers while visualize a space in the vessel wall.

15. A method for imaging a vessel wall during a dissection of the vessel wall, the method comprising:

positioning an end effector assembly adjacent to a target region of the vessel wall, wherein the end effector assembly comprises an exit port positioned to direct a tissue access component and a tissue dissection component toward a vessel wall when the end effector assembly is adjacent to the target region;

positionally coupling an imaging transducer to the tissue access component such that the imaging transducer advances within a transducer lumen at the end effector assembly simultaneously with the tissue access component advancing through the exit port;

advancing the imaging transducer within the transducer lumen while the tissue access component advances through the exit port and into the vessel wall;

obtaining images from the imaging transducer while advancing the imaging transducer to visualize the vessel wall while the tissue access component creates a space in the vessel wall;

positionally coupling the imaging transducer to the tissue dissection component such that the imaging transducer advances simultaneously with the tissue dissection component;

advancing the imaging transducer within the transducer lumen while the tissue dissection component advances through the exit port and into the space in the vessel wall; and obtaining images from the imaging transducer while advancing the imaging transducer to visualize the vessel wall during the dissection.

16. The method of claim 15, further comprising obtaining images of the vessel wall from the imaging transducer while positioning the end effector assembly to visualize the target region in the vessel wall.

17. The method of claim 15 wherein the tissue dissection component is configured to slide concentrically over the tissue access component, and wherein the method further comprises advancing the tissue dissection component concentrically over the tissue access component to position the tissue dissection component within the space in the vessel wall.

* * * * *